United States Patent
Lee et al.

(10) Patent No.: US 8,257,386 B2
(45) Date of Patent: *Sep. 4, 2012

(54) SURGICAL INSTRUMENT

(75) Inventors: Woojin Lee, Hopkinton, MA (US);
Andres Chamorro, Natick, MA (US);
Richard Ross, South Richford, VT (US);
Marvin A. Guiles, Stow, MA (US);
Eileen M. Heneberry, Westwood, MA (US); James C. Hollenbeck, Brighton, MA (US)

(73) Assignee: Cambridge Endoscopic Devices, Inc., Framingham, MA (US)

( * ) Notice: Subject to any disclaimer, the term of this patent is extended or adjusted under 35 U.S.C. 154(b) by 1196 days.

This patent is subject to a terminal disclaimer.

(21) Appl. No.: 11/900,417

(22) Filed: Sep. 11, 2007

(65) Prior Publication Data
US 2009/0069842 A1 Mar. 12, 2009

(51) Int. Cl.
*A61B 17/00* (2006.01)
(52) U.S. Cl. .................................................. 606/205
(58) Field of Classification Search .......... 606/139–146, 606/205
See application file for complete search history.

(56) References Cited

U.S. PATENT DOCUMENTS

| | | | |
|---|---|---|---|
| 2,028,635 A | 1/1936 | Wappler | |
| 2,507,710 A | 5/1950 | Grosso | |
| 2,513,027 A * | 6/1950 | Kruczek | 248/181.1 |
| 2,790,437 A | 4/1957 | Moore | |
| 3,557,780 A | 1/1971 | Sato | |
| 3,858,577 A | 1/1975 | Bass et al. | |
| 3,895,636 A | 7/1975 | Schmidt | |
| 4,483,562 A | 11/1984 | Schoolman | |
| 4,688,554 A | 8/1987 | Habib | |
| 4,728,020 A | 3/1988 | Green et al. | |
| 4,763,669 A | 8/1988 | Jaeger | |
| 4,872,456 A | 10/1989 | Hasson | |
| 4,880,015 A | 11/1989 | Nierman | |
| 4,944,093 A | 7/1990 | Falk | |
| 4,944,741 A | 7/1990 | Hasson | |
| 4,945,920 A | 8/1990 | Clossick | |
| 5,002,543 A | 3/1991 | Bradshaw et al. | |
| 5,042,707 A | 8/1991 | Taheri | |

(Continued)

FOREIGN PATENT DOCUMENTS
EP 0 095 970 A2 12/1983
(Continued)

OTHER PUBLICATIONS

Nakamura et al., Multi-DOF Forceps Manipulator System for Laparoscopic Surgery—Mechanism Miniaturized & Evaluation of New Enterfaces, 5 pgs.

(Continued)

*Primary Examiner* — Gary Jackson
*Assistant Examiner* — Eric Blatt
(74) *Attorney, Agent, or Firm* — David M. Driscoll, Esq.

(57) ABSTRACT

A medical instrument having a proximal control handle and a distal tool that are intercoupled by an elongated instrument shaft that is meant to pass internally of an anatomic body, proximal and distal movable members that respectively intercouple the proximal control handle and the distal tool with the instrument shaft, cable control means disposed between the movable members, an actuation member at the handle for controlling the distal tool through the movable members, and a coupler for selectively engaging or disengaging separable cable segments of the actuation member.

33 Claims, 20 Drawing Sheets

U.S. PATENT DOCUMENTS

| | | |
|---|---|---|
| 5,209,747 A | 5/1993 | Knoepfler |
| 5,271,381 A | 12/1993 | Ailinger et al. |
| 5,273,026 A | 12/1993 | Wilk |
| 5,275,608 A | 1/1994 | Forman et al. |
| 5,314,424 A | 5/1994 | Nicholas |
| 5,330,502 A | 7/1994 | Hassler et al. |
| 5,344,428 A | 9/1994 | Griffiths |
| 5,383,880 A | 1/1995 | Hooven |
| 5,386,818 A | 2/1995 | Schneebaum et al. |
| 5,395,367 A | 3/1995 | Wilk |
| 5,405,344 A | 4/1995 | Williamson et al. |
| 5,433,721 A | 7/1995 | Hooven et al. |
| 5,441,494 A | 8/1995 | Ortiz |
| 5,454,827 A | 10/1995 | Aust et al. |
| 5,501,654 A | 3/1996 | Failla et al. |
| 5,520,678 A | 5/1996 | Heckele et al. |
| 5,599,151 A | 2/1997 | Daum et al. |
| 5,618,294 A | 4/1997 | Aust et al. |
| 5,643,294 A | 7/1997 | Tovey et al. |
| 5,702,408 A | 12/1997 | Wales et al. |
| 5,759,151 A | 6/1998 | Sturges |
| 5,766,196 A | 6/1998 | Griffiths |
| 5,772,578 A | 6/1998 | Heimberger et al. |
| 5,823,066 A | 10/1998 | Huitema et al. |
| 5,827,177 A | 10/1998 | Oneda et al. |
| 5,851,208 A | 12/1998 | Trott |
| 5,855,569 A | 1/1999 | Komi |
| 5,873,817 A | 2/1999 | Kokish et al. |
| 5,899,425 A | 5/1999 | Corey, Jr. et al. |
| 5,899,914 A | 5/1999 | Zirps et al. |
| 5,904,647 A | 5/1999 | Ouchi |
| 5,916,146 A | 6/1999 | Allotta et al. |
| 5,916,147 A | 6/1999 | Boury |
| 5,921,694 A * | 7/1999 | Herbermann .................. 403/56 |
| 5,921,956 A | 7/1999 | Grinberg et al. |
| 5,928,263 A | 7/1999 | Hoogeboom |
| 5,938,678 A | 8/1999 | Zirps et al. |
| 5,944,713 A | 8/1999 | Schuman |
| 6,126,633 A | 10/2000 | Kaji et al. |
| 6,174,280 B1 | 1/2001 | Oneda et al. |
| 6,210,377 B1 | 4/2001 | Ouchi |
| 6,210,378 B1 | 4/2001 | Ouchi |
| 6,270,453 B1 | 8/2001 | Sakai |
| 6,551,238 B2 | 4/2003 | Staud |
| 6,595,984 B1 | 7/2003 | DeGuillebon |
| 6,623,424 B2 | 9/2003 | Hayakawa et al. |
| 6,638,214 B2 | 10/2003 | Akiba |
| 6,656,195 B2 | 12/2003 | Peters et al. |
| 6,666,854 B1 | 12/2003 | Lange |
| 6,752,756 B2 | 6/2004 | Lunsford et al. |
| 6,761,717 B2 | 7/2004 | Bales et al. |
| 7,025,775 B2 | 4/2006 | Gadberry et al. |
| 7,090,637 B2 | 8/2006 | Danitz |
| 7,147,650 B2 | 12/2006 | Lee |
| 2002/0045803 A1 | 4/2002 | Abe et al. |
| 2002/0095175 A1 | 7/2002 | Brock et al. |
| 2002/0133173 A1 | 9/2002 | Brock et al. |
| 2002/0156497 A1 | 10/2002 | Nagase et al. |
| 2002/0177750 A1 | 11/2002 | Pilvisto |
| 2002/0177847 A1 | 11/2002 | Long |
| 2003/0065359 A1 | 4/2003 | Weller et al. |
| 2003/0109898 A1 | 6/2003 | Schwarz et al. |
| 2003/0135204 A1 | 7/2003 | Lee et al. |
| 2003/0149338 A1 | 8/2003 | Francois et al. |
| 2003/0191494 A1 | 10/2003 | Gray et al. |
| 2003/0216618 A1 | 11/2003 | Arai |
| 2004/0049205 A1 | 3/2004 | Lee et al. |
| 2004/0111009 A1 | 6/2004 | Adams et al. |
| 2004/0138529 A1 | 7/2004 | Wiltshire et al. |
| 2004/0176751 A1 | 9/2004 | Weitzner et al. |
| 2004/0193146 A1 | 9/2004 | Lee et al. |
| 2004/0236316 A1 | 11/2004 | Danitz et al. |
| 2005/0049580 A1 | 3/2005 | Brock et al. |
| 2005/0107667 A1 | 5/2005 | Danitz et al. |
| 2005/0125027 A1 * | 6/2005 | Knodel et al. ................ 606/205 |
| 2005/0228440 A1 | 10/2005 | Brock et al. |
| 2005/0251112 A1 | 11/2005 | Danitz et al. |
| 2005/0273084 A1 | 12/2005 | Hinman et al. |
| 2005/0273085 A1 | 12/2005 | Hinman et al. |
| 2006/0020287 A1 | 1/2006 | Lee et al. |
| 2006/0195097 A1 | 8/2006 | Evans et al. |
| 2006/0206101 A1 | 9/2006 | Lee |
| 2006/0270909 A1 | 11/2006 | Davis et al. |
| 2007/0003385 A1 * | 1/2007 | Zepic et al. .................. 408/141 |
| 2007/0250110 A1 | 10/2007 | Lu et al. |

FOREIGN PATENT DOCUMENTS

| | | |
|---|---|---|
| EP | 0 448 284 A2 | 9/1991 |
| EP | 0 626 604 A2 | 5/1994 |
| EP | 0 427 949 B1 | 6/1994 |
| EP | 1 620 164 | 11/2007 |
| GB | 2 143 920 | 2/1985 |
| WO | WO 90/05491 | 5/1990 |
| WO | WO 92/01414 | 2/1992 |
| WO | WO 94/17965 | 8/1994 |

OTHER PUBLICATIONS

Ryoichi Nakamura et al., Multi-DOF Manipulator System for Laparoscopic Surgery, 8 pgs.

Ryoichi Nakamura et al., Development of Forceps Manipulator System for Laparoscopic Surgery, 6 pgs.

Hiromasa Yamashita et al., "Multi-Slider Linkage Mechanism for Endoscopic Forceps Manipulator," In Proc. of the 2003 IEEE/RSJ, Intl. Conference on Intelligent Robots and Systems, vol. 3, pp. 2577-2582, Las Vegas, Nevada, Oct. 2003.

* cited by examiner

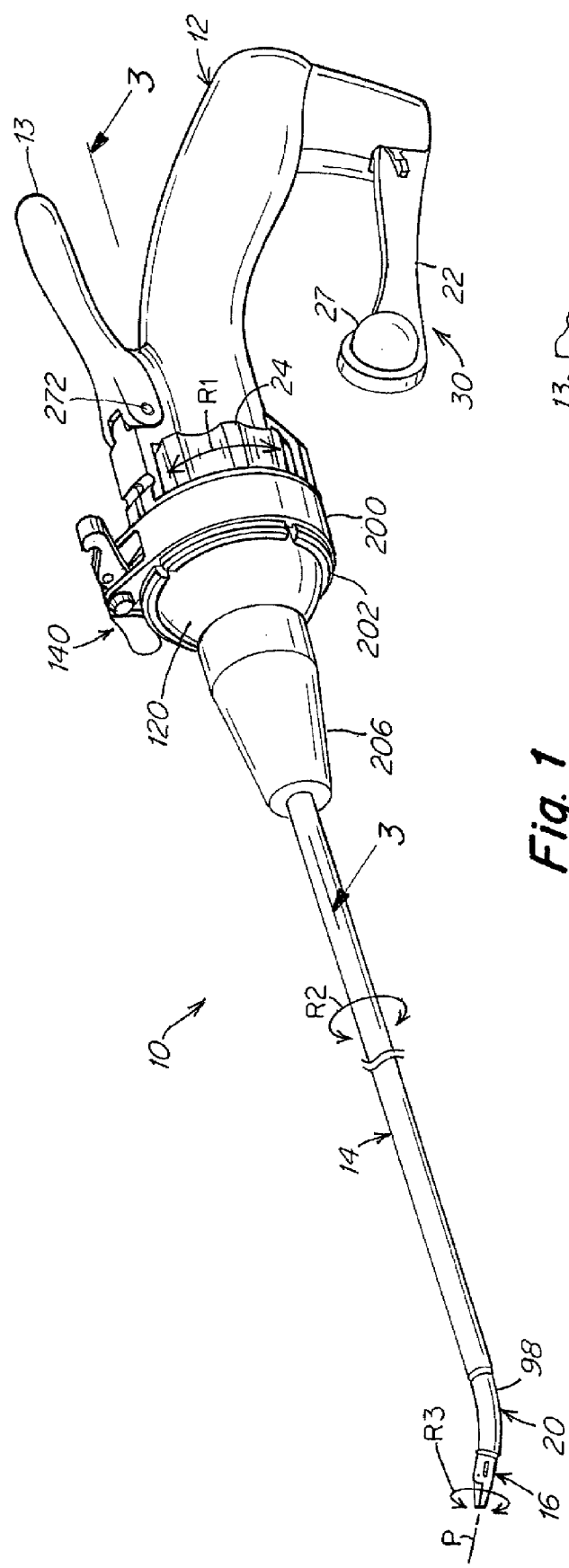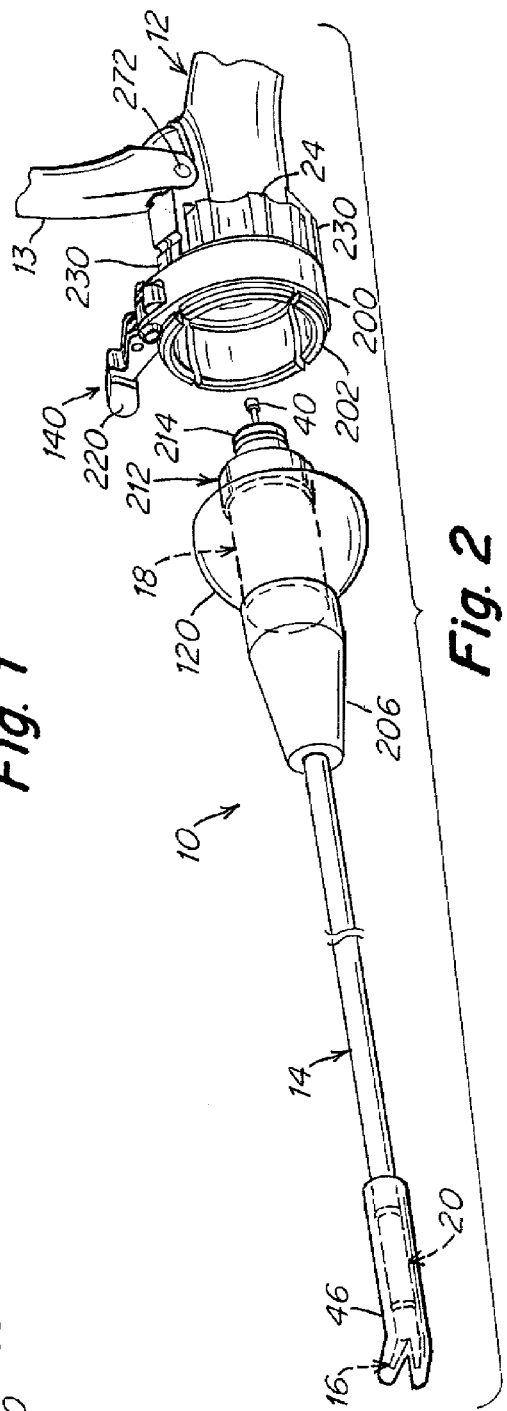

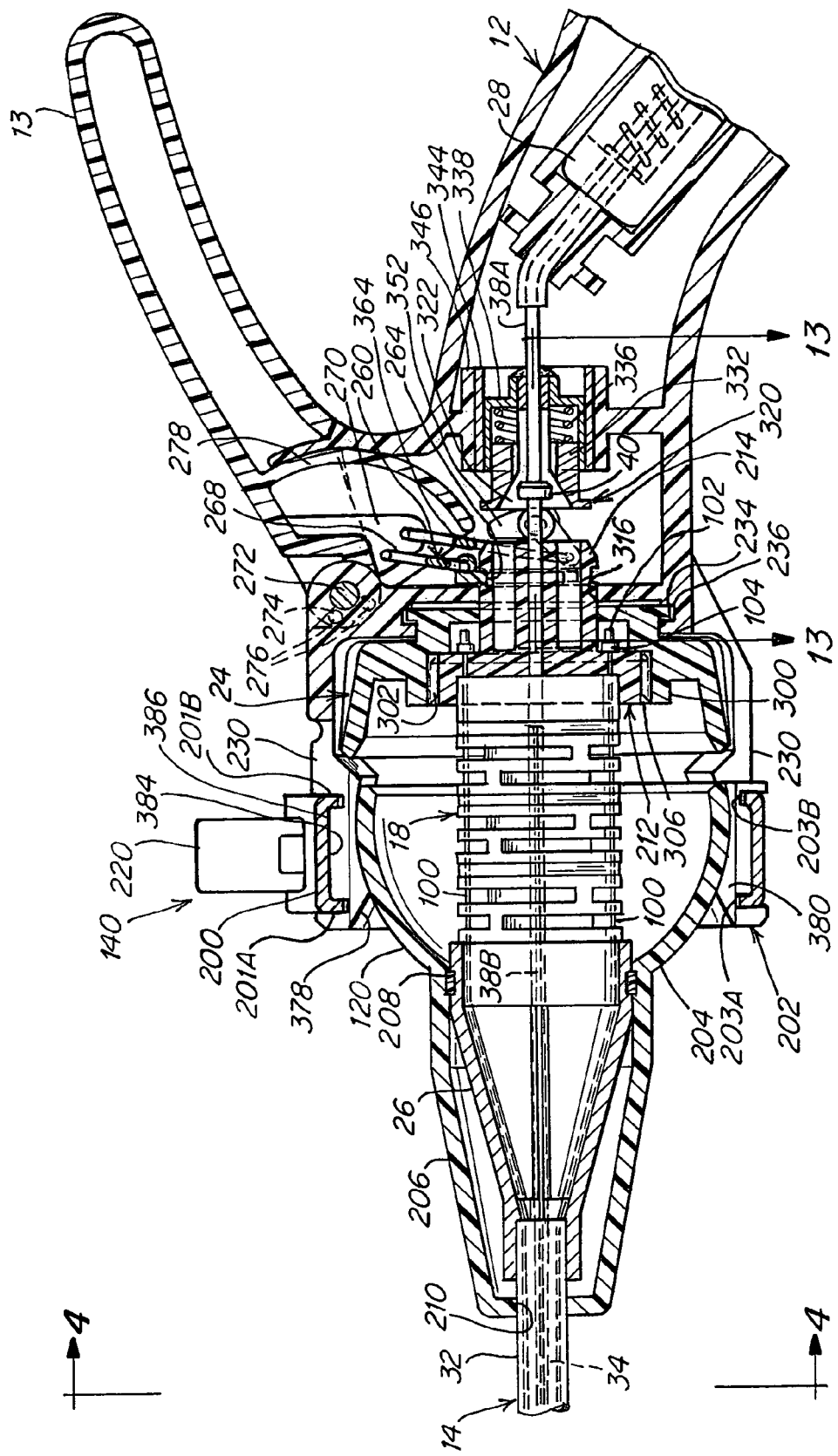

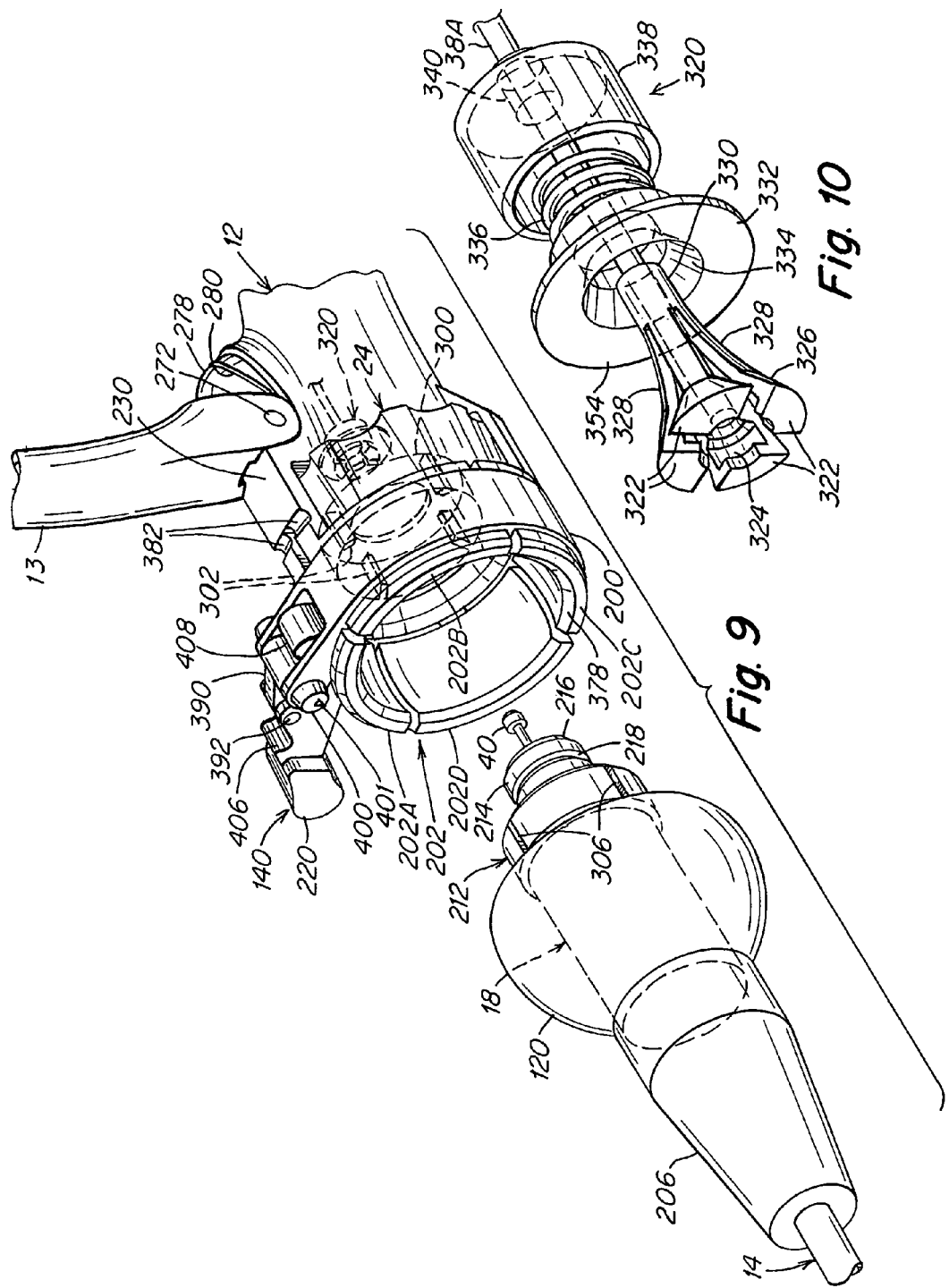

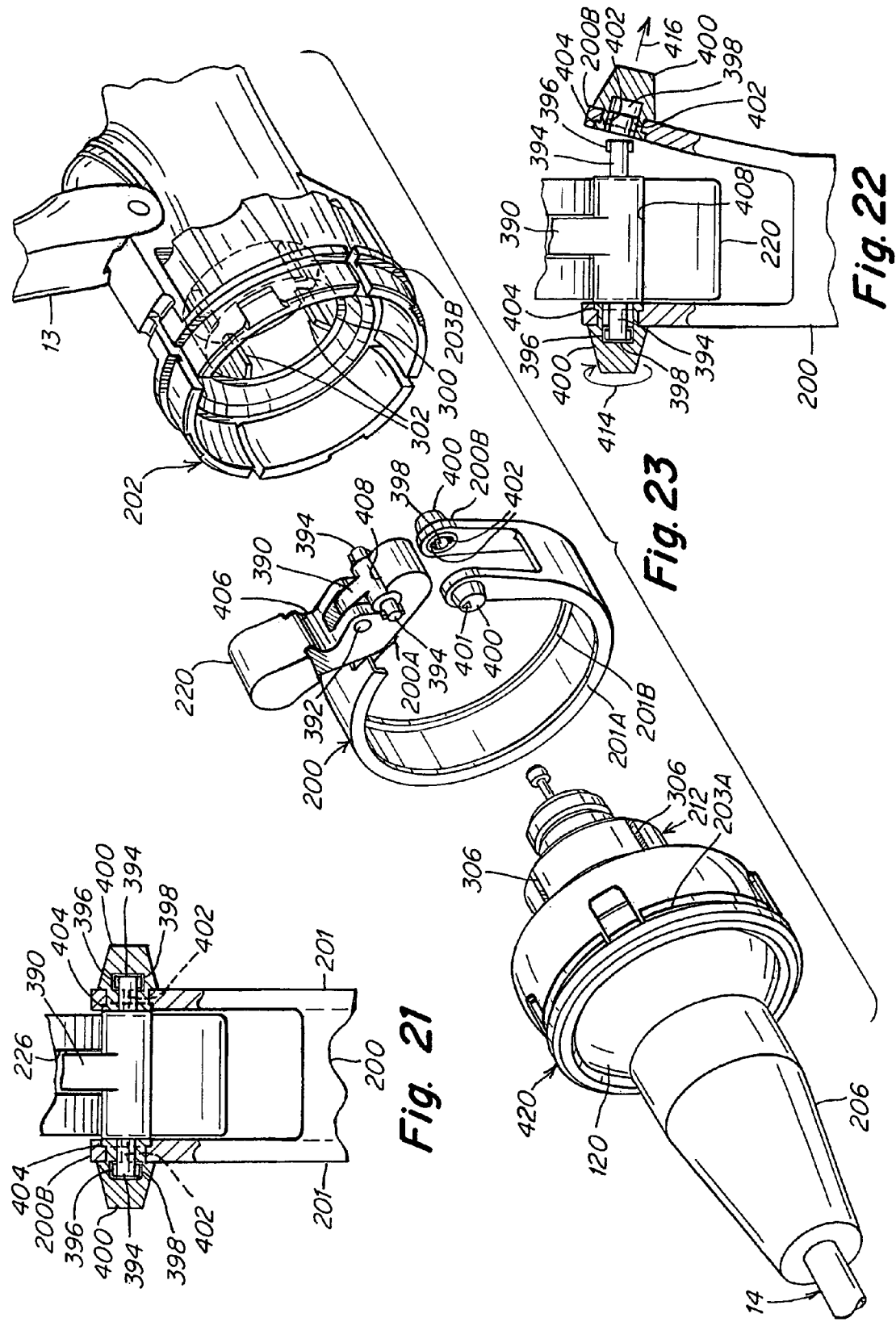

SURGICAL INSTRUMENT

TECHNICAL FIELD

The present invention relates in general to medical instruments, and more particularly to manually-operated surgical instruments that are intended for use in minimally invasive surgery or other forms of surgical or medical procedures or techniques. The instrument described herein is primarily for a laparoscopic procedure, however, it is to be understood that the instrument of the present invention can be used for a wide variety of other procedures, including intraluminal procedures.

BACKGROUND OF THE INVENTION

Endoscopic and laparoscopic instruments currently available in the market are extremely difficult to learn to operate and use, mainly due to a lack of dexterity in their use. For instance, when using a typical laparoscopic instrument during surgery, the orientation of the tool of the instrument is solely dictated by the location of the target and the incision. These instruments generally function with a fulcrum effect using the patients own incision area as the fulcrum. As a result, common tasks such as suturing, knotting and fine dissection have become challenging to master. Various laparoscopic instruments have been developed over the years to overcome this deficiency, usually by providing an extra articulation often controlled by a separately disposed control member for added control. However, even so these instruments still do not provide enough dexterity to allow the surgeon to perform common tasks such as suturing, particularly at any arbitrarily selected orientation. Also, existing instruments of this type do not provide an effective way to hold the instrument in a particular position. Moreover, existing instruments require the use of both hands in order to effectively control the instrument.

An improved instrument is shown in U.S. Pat. No. 7,147,650 having enhanced dexterity and including, inter alia, a rotation feature with proximal and distal bendable members. Even though this instrument has improved features there remains the need for a more economically feasible instrument, and one in which the handle can be re-used while the tip of the instrument is disposable or reposable.

Accordingly, an object of the present invention is to provide an improved laparoscopic or endoscopic instrument in which a portion of the instrument is re-useable and a portion is disposable. In embodiments described herein the handle end of the instrument is re-useable and the distal portion or tip of the instrument is disposable. By being able to re-use the handle portion, the instrument is more economically feasible.

A further object of the present invention is to provide an improved laparoscopic or endoscopic surgical instrument that allows the surgeon to manipulate the tool end of the surgical instrument with greater dexterity.

Another object of the present invention is to provide an improved surgical or medical instrument that has a wide variety of applications, through incisions, through natural body orifices or intraluminally.

Another object of the present invention is to provide a locking feature that is an important adjunct to the other controls of the instrument enabling the surgeon to lock the instrument once in the desired position. This makes it easier for the surgeon to thereafter perform surgical procedures without having to, at the same time, hold the instrument in a particular bent configuration.

Still another object of the present invention is to provide an improved medical instrument that can be effectively controlled with a single hand of the user.

Still another object of the present invention is to provide an improved medical instrument that is characterized by the ability to lock the position of the instrument in a pre-selected position while enabling rotation of the tip of the instrument while locked.

SUMMARY OF THE INVENTION

To accomplish the foregoing and other advantages and features of the present invention there is provided a surgical instrument comprising: an instrument shaft having proximal and distal ends; a tool disposed from the distal end of the instrument shaft; a control handle coupled from the proximal end of the instrument shaft; a distal motion member for coupling the distal end of the instrument shaft to the distal tool; a proximal motion member for coupling the proximal end of the instrument shaft to the handle; actuation means extending between the distal and proximal motion members for coupling motion of the proximal motion member to the distal motion member for controlling the positioning of the tool; and an actuation cable extending from the handle to the tool for controlling the actuation of the tool. The actuation cable is separated into two inter-engagable cable segments that enable the proximal motion member to be disconnected from the control handle.

In accordance with other aspects of the present invention the surgical instrument may further include a rotation means disposed adjacent the control handle and rotatable relative to the control handle for causing a corresponding rotation of the instrument shaft and tool; at least the proximal motion member may comprise a proximal bendable member, the rotation means may comprise a rotation knob that is adapted to rotate the tool about a distal tool roll axis and the rotation knob may be disposed between the control handle and proximal bendable member; an actuation lever may be supported from the handle at a pivot point on the handle and for controlling the actuation cable; a slider may be provided for capturing the proximal end of said tool actuation cable and an actuation lever supported at the handle for controlling the translation of the slider and, in turn, the operation of the tool; a locking mechanism may be provided for fixing the position of the tool at a selected position and having locked and unlocked states, the locking mechanism including a ball and socket arrangement disposed about the proximal motion member and a cinch member for locking the ball and socket arrangement; the socket member may comprise a split socket and the cinch member closes the split socket to lock the socket on the ball; a horn may be provided that is pivotally supported from the handle and that is operable to engage and disengage the cable segments; and a collet may be supported in the handle for closing about the cable segments.

In accordance with another embodiment of the invention there is provided a medical instrument having a proximal control handle and a distal tool that are intercoupled by an elongated instrument shaft that is meant to pass internally of an anatomic body, proximal and distal movable members that respectively intercouple the proximal control handle and the distal tool with the instrument shaft, cable control means disposed between the movable members, an actuation member at the handle for controlling the distal tool through the movable members, and a coupler for selectively engaging or disengaging separable cable segments of the actuation member.

In related aspects of the present invention the coupler may include a collet attached to one of the cable segments and a capture lug on the other of the cable segments, the collet for retaining the capture lug to engage the cable segments; a pivot member may be provided on the handle including at least one link that is operable to control a cam that sets open and closed positions of the collet; the pivot member may be in the form of a horn at the top of the handle to assist in a comfort grip of the handle; and collet may include a quick disconnect mechanism having a base in which the collet is positioned and a spring that biases the base to a closed position of the collet.

In accordance with still another embodiment of the invention there is provided a method of controlling a medical instrument that has a proximal end including a control handle and a distal end including a distal tool, with the control handle and distal tool being intercoupled by an elongated instrument shaft and the tool actuated from a tool control cable. The method includes providing proximal and distal movable members that respectively intercouple the proximal control handle and the distal tool with the instrument shaft, the proximal and distal movable members being intercoupled so that a motion at the proximal movable member controls the distal movable member, dividing the tool control cable into separate cable segments and interlocking the separate cable segments so that the tool control cable is operable. A further step may include manually controlling, from the proximal end of the instrument, the rotation of the distal tool about its longitudinal distal tool axis.

In accordance with another embodiment of the invention there is provided an instrument having a proximal control handle and a distal tool that are intercoupled by an elongated instrument shaft, proximal and distal movable members that respectively intercouple the proximal control handle and the distal tool with the instrument shaft, means disposed between the movable members so that a motion at the proximal movable member controls the distal movable member and, in turn, the distal tool, means supported at the handle for controlling the distal tool including a tool control cable that extends between the handle and distal tool, the tool control cable including separate control cable segments that are adapted to have one of an engaged state and a disengaged state.

In accordance with still other aspects of the present invention there is provided a control member at the control handle and manipulable by a user to control, via the proximal and distal movable members, the rotation of the distal tool about its distal tool axis; the proximal motion member can be disconnected from the control handle when the control cable segments are in their dis-engaged state; including a coupler for selectively engaging or disengaging the separable cable segments; wherein the coupler may include a collet attached to one of the cable segments and a capture lug on the other of the cable segments, the collet for retaining the capture lug to engage the cable segments; and wherein the collet may include a quick disconnect mechanism having a base in which the collet is positioned and a spring that biases the base to a closed position of the collet.

DESCRIPTION OF THE DRAWINGS

Numerous other advantages can be realized in accordance with the present invention by referring to the accompanying drawings, in which:

FIG. 1 is a perspective view of a first embodiment of a surgical instrument constructed in accordance with the present invention with a disposable shaft portion and a reusable handle portion;

FIG. 2 is a fragmentary exploded perspective view of the instrument and shaft of FIG. 1;

FIG. 3 is a partial cross-sectional side view of the instrument as taken along line 3-3 of FIG. 1 and with the instrument in an engaged or locked position;

FIG. 9 is a fragmentary exploded perspective detail view of the instrument on a somewhat enlarged scale;

FIG. 10 is an exploded perspective view of one embodiment of a coupling means for the end effector actuation cable;

FIG. 21 is a fragmentary cross-sectional view of a means to detach the cinch ring as taken along line 21-21 of FIG. 18;

FIG. 22 is a cross-sectional view similar to that illustrated in FIG. 21 and showing the cinch ring partially detached;

FIG. 23 is a fragmentary exploded perspective view of a fourth embodiment of a means to attach the instrument shaft to the handle portion;

DETAILED DESCRIPTION

Figure 4:
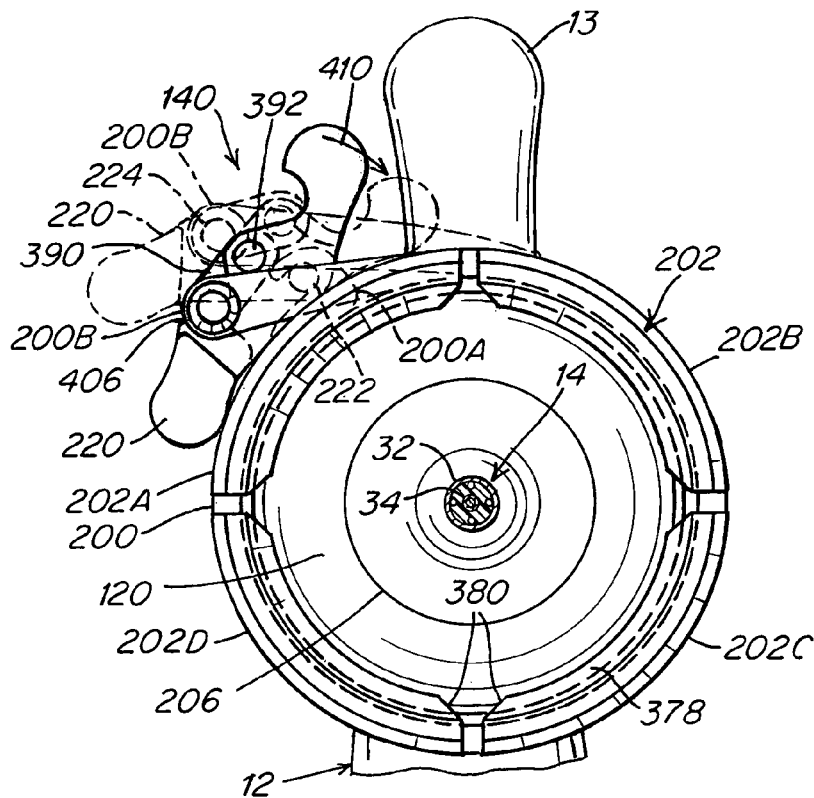
FIG. 4 is a cross-sectional end view of the instrument taken along line 4-4 of FIG. 3 showing a locked and a first released position of the cinch ring.

The present invention is illustrated in the drawings as a surgical instrument that has two portions such that a detachable instrument shaft portion may be disposable and a re-usable handle portion may be sterilized and reused numerous times. This allows for a higher quality instrument handle portion while keeping the overall price of the instrument reasonable.

The instrument of the present invention may be used to perform minimally invasive procedures. "Minimally invasive procedure," refers herein to a surgical procedure in which a surgeon operates through a small cut or incision, the small incision being used to access the operative site. In one embodiment, the incision length ranges from 1 mm to 20 mm in diameter, preferably from 5 mm to 10 mm in diameter. This procedure contrasts those procedures requiring a large cut to access the operative site. Thus, the flexible instrument is preferably used for insertion through such small incisions and/or through a natural body lumen or cavity, so as to locate the instrument at an internal target site for a particular surgical or medical procedure. The introduction of the surgical instrument into the anatomy may also be by percutaneous or surgical access to a lumen, vessel or cavity, or by introduction through a natural orifice in the anatomy.

In addition to use in a laparoscopic procedure, the instrument of the present invention may be used in a variety of other medical or surgical procedures including, but not limited to, colonoscopic, upper GI, arthroscopic, sinus, thoracic, prostate, transvaginal, orthopedic and cardiac procedures. Depending upon the particular procedure, the instrument shaft may be rigid, semi-rigid or flexible.

Although reference is made herein to a "surgical instrument," it is contemplated that the principles of this invention also apply to other medical instruments, not necessarily for surgery, and including, but not limited to, such other implements as catheters, as well as diagnostic and therapeutic instruments and implements.

There are a number of unique features embodied in the instrument that is described herein. For example, there is provided a locking mechanism that is constructed using a ball and socket arrangement disposed about the proximal motion member that follows the bending action and in which an annular cinch ring is used to retain the ball and socket arrangement in a fixed particular position, and thus also maintain the proximal and distal bendable members in a particular bent condition, or in other words locked in that position. The cinch ring includes a locking lever that is conveniently located adjacent to the instrument handle and that is easily manipulated to lock and unlock the cinch ring and, in turn, the position of the end effector. The cinch ring is also preferably rotatable to that the locking lever can be positioned conveniently or can be switched (rotated) between left and right handed users. This lock control allows the surgeon one less degree of freedom to concentrate on when performing certain tasks. By locking the bendable sections at a particular position, this enables the surgeon to be more hands-free for controlling other degrees of freedom of the instrument such as manipulation of the rotation knob to, in turn, control the orientation of the end effector.

A main feature of the present invention relates to the ability of the instrument to be partially disposable and partially re-useable. In that way the instrument cost can be substantially reduced as it is not necessary to replace the entire instrument for each procedure. In one embodiment a disconnect means is provided at the handle where the distal motion member, tool, instrument shaft and proximal motion member are separable from the handle of the instrument. This enables the distal components to be engageable and dis-engageable from the handle. The handle portion of the instrument is re-useable and thus the cost of that part of the instrument is essentially spread over several instrument uses.

FIG. 1 is a perspective view of one embodiment of the surgical instrument 10 of the present invention. In this surgical instrument both the tool and handle motion members or bendable members are capable of bending in any direction. They are interconnected via cables (preferably four cables) in such a way that a bending action at the proximal member provides a related bending at the distal member. The proximal bending is controlled by a motion or deflection of the control handle by a user of the instrument. In other words the surgeon grasps the handle and once the instrument is in position any motion (deflection) at the handle immediately controls the proximal bendable member which, in turn, via cabling controls a corresponding bending or deflection at the distal bendable member. This action, in turn, controls the positioning of the distal tool.

The proximal bendable member is preferably generally larger than the distal bendable member so as to provide enhanced ergonomic control. In the illustrated embodiment the ratio of proximal to distal bendable member diameters may be on the order of three to one. In one version in accordance with the invention there may be provided a bending action in which the distal bendable member bends in the same direction as the proximal bendable member. In an alternate embodiment the bendable, turnable or flexible members may be arranged to bend in opposite directions by rotating the actuation cables through 180 degrees, or could be controlled to bend in virtually any other direction depending upon the relationship between the distal and proximal support points for the cables.

As has been noted, the amount of bending motion produced at the distal bending member is determined by the dimension of the proximal bendable member in comparison to that of the distal bendable member. In the embodiment described the proximal bendable member is generally larger than the distal bendable member, and as a result, the magnitude of the motion produced at the distal bendable member is greater than the magnitude of the motion at the proximal bendable member. The proximal bendable member can be bent in any direction (about 360 degrees) controlling the distal bendable member to bend in either the same or an opposite direction, but in the same plane at the same time. Also, as depicted in FIG. 1, the surgeon is able to bend and roll the instrument's tool about its longitudinal axis to any orientation simply by rolling the axial rotation knob 24 about a rotation direction indicated in FIG. 1 by the rotation arrow R1.

In this description reference is made to bendable members. These members may also be referred to as turnable members, bendable sections or flexible members. In the descriptions set out herein, terms such as "bendable section," "bendable segment," "bendable member," or "turnable member" refer to an element of the instrument that is controllably bendable in comparison to an element that is pivoted at a joint. The term "movable member" is considered as generic to bendable sections and joints. The bendable elements of the present invention enable the fabrication of an instrument that can bend in any direction without any singularity and that is further characterized by a ready capability to bend in any direction, all preferably with a single unitary or uni-body structure. A definition of a "unitary" or "uni-body" structure is—a structure that is constructed only of a single integral member and not one that is formed of multiple assembled or mated components—.

A definition of these bendable members is—an instrument element, formed either as a controlling means or a controlled means, and that is capable of being constrained by tension or compression forces to deviate from a straight line to a curved configuration without any sharp breaks or angularity—. Bendable members may be in the form of unitary structures, such as of the type shown herein in FIG. 3 for the proximal bendable member, may be constructed of engageable discs, or the like, may include bellows arrangements or may comprise a movable ring assembly. For several forms of bendable members refer to co-pending applications Ser. No. 11/185,911 filed on Jul. 20, 2005; Ser. No. 11/505,003 filed on Aug. 16, 2006 and Ser. No. 11/523,103 filed on Sep. 19, 2006, all of which are hereby incorporated by reference herein in their entirety.

FIG. 1 shows a preferred embodiment of the instrument of the present invention. Further details are illustrated in FIGS. 2 through 14. FIG. 1 depicts the surgical instrument 10 in a perspective view, as may occur during a surgical procedure. For example, the instrument may be used for laparoscopic surgery through the abdominal wall. For this purpose there is provided an insertion site at which there is disposed a cannula or trocar. The shaft 14 of the instrument 10 is adapted to pass through the cannula or trocar so as to dispose the distal end of the instrument at the operative site. The end effector 16 is depicted in FIG. 1. The embodiment of the instrument shown in FIG. 1 is typically used with a sheath 98 covering the distal member 20 to keep bodily fluids from entering the distal bending member 20. The shaft 14 includes an outer shaft tube 32 and an inner shaft tube 34 as in previous applications incorporated herein.

FIG. 2 shows a separate sheath 46 that is temporarily used to cover the entire distal bendable member and end effector. This sheath 46 is only used for shipping the instrument and may be discarded once the instrument is in place on the handle. The sheath 46 keeps the jaws in an open position, as illustrated in FIG. 2, and also keeps the distal bendable member in a substantially straight position. By doing that the actuation cable is maintained in a particular aligned position and ready for engagement with the handle portion of the instrument. Instead of using a pre-formed sheath one may alternatively use a biasing means in the instrument to maintain a predetermined position of the instrument cable, usually one in which the jaws are maintained open.

A rolling motion can be carried out with the instrument of the present invention. This can occur by virtue of the rotation of the rotation knob 24 relative to the handle 12 about a longitudinal shaft axis. This is represented in FIG. 1 by the rotation arrow R1. When the rotation knob 24 is rotated, in either direction, this causes a corresponding rotation of the instrument shaft 14. This is depicted in FIG. 1 by the rotational arrow R2. This same motion also causes a rotation of the distal bendable member and end effector 16 about an axis that corresponds to the instrument tip, depicted in FIG. 1 as about the longitudinal tip or tool axis P. In FIG. 1 refer to the rotational arrow R3 at the tip of the instrument.

Any rotation of the rotation knob 24 while the instrument is locked (or unlocked) maintains the instrument tip at the same angular position, but rotates the orientation of the tip (tool). For a further explanation of the tip rotational feature refer to co-pending application Ser. No. 11/302,654, filed on Dec. 14, 2005, particularly FIGS. 25-28, which is hereby incorporated by reference in its entirety.

The handle 12, via proximal bendable member 18, may be tilted at an angle to the instrument shaft longitudinal center axis. This tilting, deflecting or bending may be considered as in the plane of the paper. By means of the cabling this action causes a corresponding bend at the distal bendable member 20 to a position wherein the tip is directed along an axis and at a corresponding angle to the instrument shaft longitudinal center axis. The bending at the proximal bendable member 18 is controlled by the surgeon from the handle 12 by manipulating the handle in essentially any direction including in and out of the plane of the paper in FIG. 1. This manipulation directly controls the bending at the proximal bendable member. For further descriptions relating to the bending refer to co-pending application Ser. No. 11/528,134 filed on Sep. 27, 2006 and Ser. No. 11/649,352 filed on Jan. 2, 2007, both of which are hereby incorporated by reference in their entirety.

Thus, the control at the handle is used to bend the instrument at the proximal motion member to, in turn, control the positioning of the distal motion member and tool. The "position" of the tool is determined primarily by this bending or motion action and may be considered as the coordinate location at the distal end of the distal motion member. Actually, one may consider a coordinate axis at both the proximal and distal motion members as well as at the instrument tip. This positioning is in three dimensions. Of course, the instrument positioning is also controlled to a certain degree by the ability of the surgeon to pivot the instrument at the incision point or at the cannula or trocar. The "orientation" of the tool, on the other hand, relates to the rotational positioning of the tool, from the proximal rotation control member, about the illustrated distal tip or tool axis P.

In the drawings a set of jaws is depicted, however, other tools or devices may be readily adapted for use with the instrument of the present invention. These include, but are not limited to, cameras, detectors, optics, scope, fluid delivery devices, syringes, etc. The tool may include a variety of articulated tools such as: jaws, scissors, graspers, needle holders, micro dissectors, staple appliers, tackers, suction irrigation tools and clip appliers. In addition, the tool may include a non-articulated tool such as: a cutting blade, probe, irrigator, catheter or suction orifice.

Figure 6:
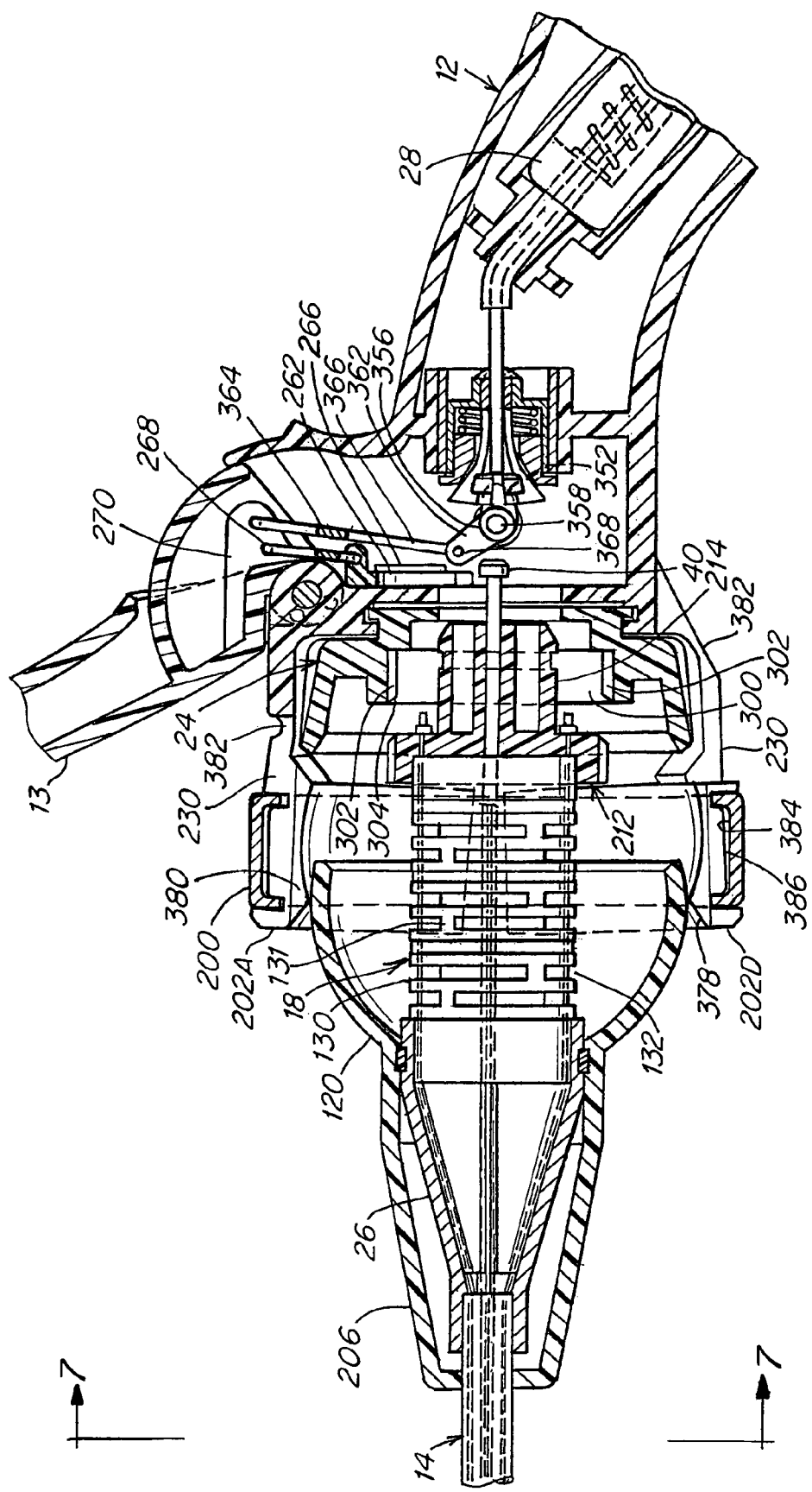
FIG. 6 is a cross-sectional view like that shown in FIG. 5 but with the instrument shaft portion being removed from the handle portion.

The surgical instrument of FIG. 1 shows a preferred embodiment of a surgical instrument 10 according to the invention in use and may be inserted through a cannula at an insertion site through a patient's skin. Many of the components shown herein, such as the instrument shaft 14, end effector 16, distal bending member 20, and proximal bending member 18 may be similar to and interact in the same manner as the instrument components described in the co-pending U.S. application Ser. No. 11/185,911 filed on Jul. 20, 2005 and hereby incorporated by reference herein in its entirety. For example, the proximal bendable member 18 is a unitary slotted structure as shown in FIG. 6 including discs 130, nibs 131 and slots 132. Many other components shown herein, particularly at the handle end of the instrument may be similar to components described in the co-pending U.S. application Ser. No. 11/528,134 filed on Sep. 27, 2006 and hereby incorporated by reference herein in its entirety. Also incorporated by reference in their entirety are U.S. application Ser. No. 10/822,081 filed on Apr. 12, 2004; U.S. application Ser. No. 11/242,642 filed on Oct. 3, 2005 and U.S. application Ser. No. 11/302,654 filed on Dec. 14, 2005, all commonly owned by the present assignee.

As illustrated in, for example, FIGS. 1-3, the control between the proximal bendable member 18 and distal bendable member 20 is provided by means of the bend control cables 100. In the illustrated embodiment four such control cables 100 may be provided in order to provide the desired all direction bending. However, in other embodiments of the present invention fewer or less numbers of bend control cables may be used. The bend control cables 100 extend through the instrument shaft 14 and through the proximal and distal bendable members. The bend control cables 100 may be constrained along substantially their entire length so as to facilitate both "pushing" and "pulling" action as discussed in further detail in the aforementioned co-pending application Ser. No. 11/649,352 filed on Jan. 2, 2007. The cables 100 may also be constrained as they pass over the conical cable guide portion of the proximal bendable member, and through the proximal bendable member itself.

The locking means interacts with the ball and socket arrangement to lock and unlock the positioning of the cables which in turn control the angle of the proximal bending member and thus the angle of the distal bendable member and end effector. This lock control allows the surgeon one less degree of freedom to concentrate on when performing certain tasks. By locking the bendable sections at a particular position, this enables the surgeon to be more hands-free for controlling other degrees of freedom of the instrument such as manipulation of the rotation knob 24 and, in turn, orientation of the end effector.

The instrument shown in FIG. 1 is considered as of a pistol grip type. However, the principles of the present invention may also apply to other forms of handles such as a straight in-line handle. In FIG. 1 there is shown a jaw clamping or actuation means 30 that is comprised mainly of the lever 22 which may have a single finger hole in the gimbaled ball 27. The ball 27 is mounted at the free end of the lever 22. The surgeon uses the ball 27 for controlling the lever 22. There may also be provided a related release function controlled either directly by the lever 22 or a separate release button. The release function is used to release the actuated or closed tool or end effector.

In the instrument that is illustrated the handle end of the instrument may be tipped or deflected in any direction as the proximal bendable member is constructed and arranged to preferably enable full 360 degree bending. This movement of the handle relative to the instrument shaft bends the instrument at the proximal bendable member 18. This action, in turn, via the bend control cables 100, bends the distal bendable member in the same direction. As mentioned before, opposite direction bending can be used by rotating or twisting the control cables through 180 degrees from one end to the other end thereof.

In the main embodiment described herein, the handle 12 is in the form of a pistol grip and includes a horn 13 to facilitate a comfortable interface between the action of the surgeon's hand and the instrument. In this embodiment the horn has the other function of providing the actuation pivot for locking and unlocking the tool control cable, as described in more detail later. The tool actuation lever 22 is shown in FIG. 1 pivotally attached at the base of the handle. The lever 22 actuates a slider 28 (see FIG. 3) that controls the tool actuation cable 38 that extends from the slider to the distal end of the instrument. The cable 38 controls the opening and closing of the jaws, and different positions of the lever control the force applied at the jaws. The cable is depicted, for example, in FIG. 8 as including proximal cable portion 38A and distal cable portion 38B.

The instrument 10 has a handle portion 12 and a detachable shaft portion 14, as shown in FIG. 1. The main components of the instrument may be like that shown in Ser. No. 11/649,352 filed on Jan. 2, 2007, particularly as to the construction of the bendable members, instrument shaft and end effector. This includes means for enabling rotation of the shaft and proximal bendable member within bearings or bearing surfaces 208 and 210 (FIG. 3). The bearing 208 interfaces between the adaptor 26 and the ball 120, while the bearing surface 210 is between the neck portion 206 and the instrument shaft. The separate portions 12 and 14, or alternatively the assembled instrument, may be sealed in a sterile package or packages prior to storage or shipping.

As shown in FIG. 2, the shaft portion 14 can be easily separated from the handle portion 12 by releasing the cinch ring 200. The shaft portion includes a shaft connector 212. The cable portion 38B is provided with an end connector lug 40. The shaft connector 212 and cable connector lug 40 are disengaged by raising the horn 13 about a pivot 272 thus enabling the shaft portion 14 and handle portion 12 to be disengaged from each other. A new shaft portion can then be easily attached to the sterilized handle by insertion and locking into the handle as described in further detail below. FIG. 1 shows the shaft and handle portions engaged which happens when the horn 13 is pivoted to the locked or down position. See also the locked position in FIG. 3.

FIG. 3 shows a somewhat schematic cross-sectional view of the connections between the shaft 14 and handle portion 12. The split hub 202 is constructed and arranged to allow the ball 120 to be pulled out of the split hub 202. The cinch ring 200 is used to lock and unlock the split hub 202, as described in more detail later. For other details of the split hub 202 refer also to FIGS. 2 and 9. The proximal bending member 18 is mounted to the shaft connector 212 that is indexed with the handle portion, and particularly with the rotation knob 24. In FIG. 3, the shaft connector 212 is shown connected to the rotation knob 24 by means of a shaft receiver portion 300 (see FIG. 8) of the rotation knob 24. The shaft connector 212 is locked into the handle portion 12 by means of the shaft locking assembly or means 260. The shaft connector is locked linearly but the assembly 260 allows rotation of the shaft portion relative to the handle portion. In FIG. 3 the jaw actuation distal cable portion 38B (see also FIG. 8) is shown terminated at the coupling lug 40. It is the coupling lug 40 that is captured by the cable coupling member or means 320 so as to in essence connect together both portions 38A and 38B of the tool actuation cable 38.

The split hub portions or petals 202A-202D each have a tapered face 378 (see FIGS. 3 and 4) so as to function as a ramp to force the petals apart when the ball 120 is pushed proximally against them during an insertion of the shaft portion into the handle portion. These inward faces or edges of the portions 202A-202D are beveled or tapered to allow easier passage of the ball. The split hub 202 is supported from the handle by means of struts 230 which are thinned as shown at 382 as illustrated in FIGS. 6 and 9 so as to function as flexible living hinges to thus allow more ready expansion of the hub petals. This structure assists in the engagement and disengagement between the shaft and handle.

Figure 7:
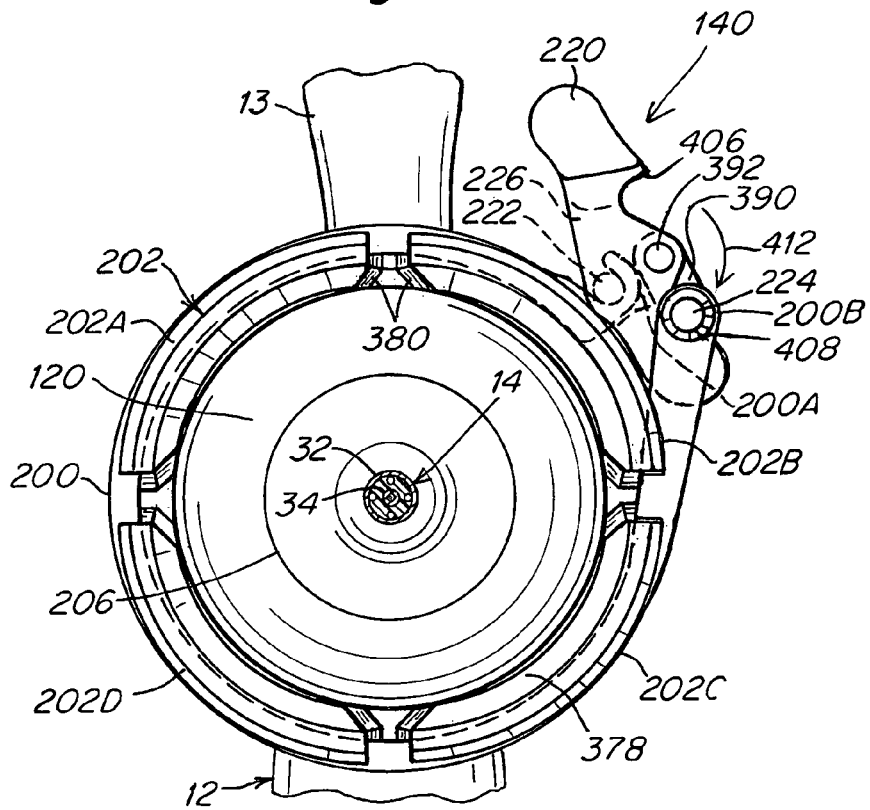
FIG. 7 is a fragmentary cross-sectional end view of the instrument taken along line 7-7 of FIG. 6 showing a rotated and a second released position of the cinch ring and the shaft ball being removed.
Figure 5:
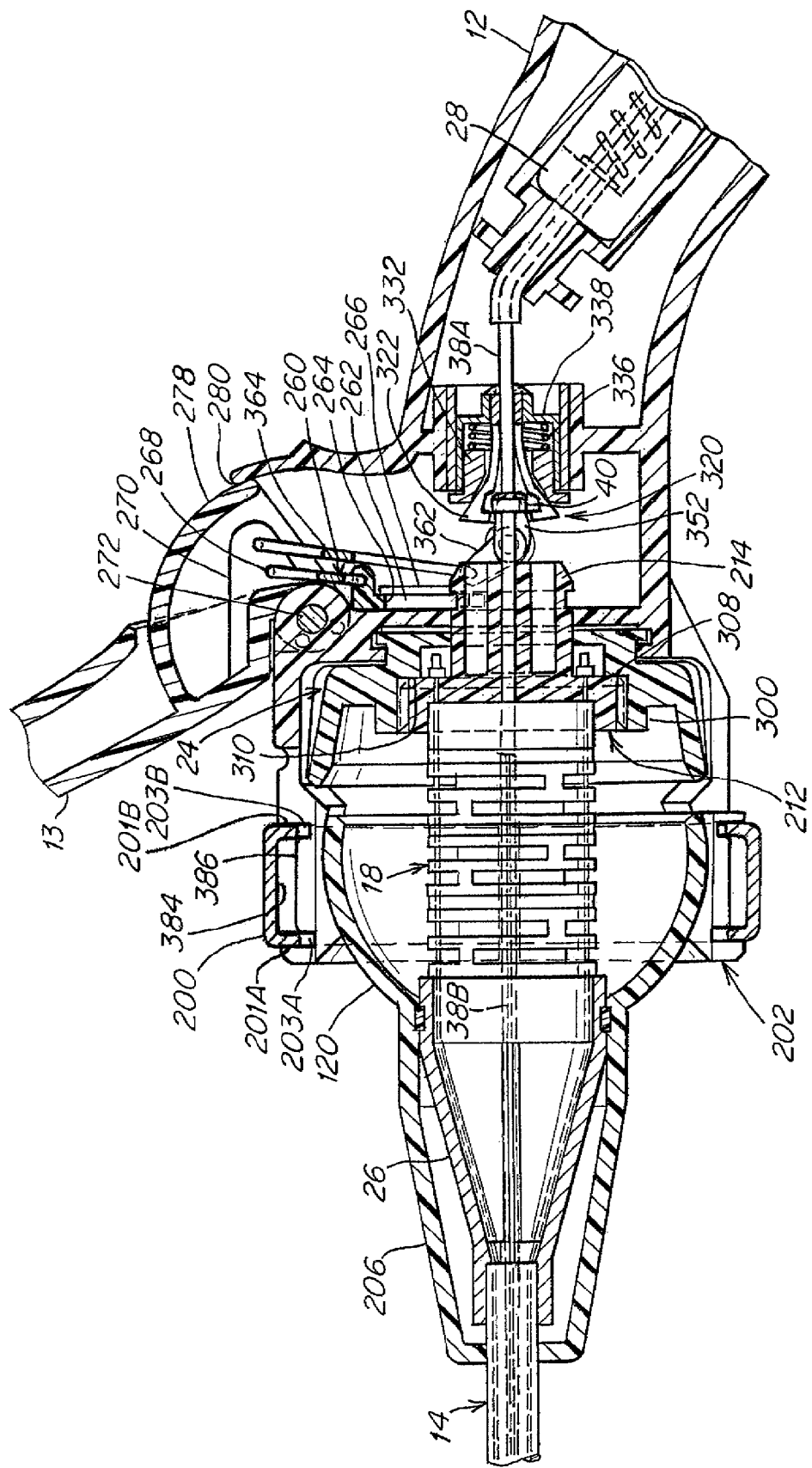
FIG. 5 is a cross-sectional view like that shown in FIG. 3 but with the instrument shaft portion being released from the handle portion and with the handle moved upwardly.

The cinch ring 200 has two flanges 201A and 201B, shown in FIG. 5 that ride in respective circumferential grooves 203A and 203B. The grooves 203A and 203B are disposed on the outer surface of the split hub 202. This interface captures the cinch ring while allowing the split hub to be separated linearly as is discussed in more detail hereinafter. The cinch ring 200 is basically controlled from the angle locking member or means 140, as shown in FIGS. 2 and 9. The angle locking member 140 is pivotally attached with the cinch ring 200. The angle locking member 140 is constructed and arranged to allow the cinch ring 200 to, not only be loosened enough to adjust the angle of the shaft relative to the handle, but to also expand to a size that is sufficient to allow enough expansion of the split hub portions to thus allow the ball 120 to be removed or inserted in the split hub 202, as illustrated in FIGS. 6 and 7. This enables the shaft portion to be dis-engaged from the handle portion.

The cinch ring flanges 201A and 201B and grooves 203A and 203B are dimensioned so that when the cinch ring 200 is loosened enough for the ball 120 to be removed from the split hub, the cinch ring 200 cannot be removed from the split hub without detaching the ends 200A and 200B of the cinch ring 200, as illustrated in the position of FIG. 23. The flanges 201 are approximately the same depth and the grooves are slightly deeper so as to not impede the pressure applied at surface 384 of the cinch ring on surface 386 of the split hub portions when the cinch ring is tightened, as in the position that is illustrated in FIG. 3.

Figure 4A:
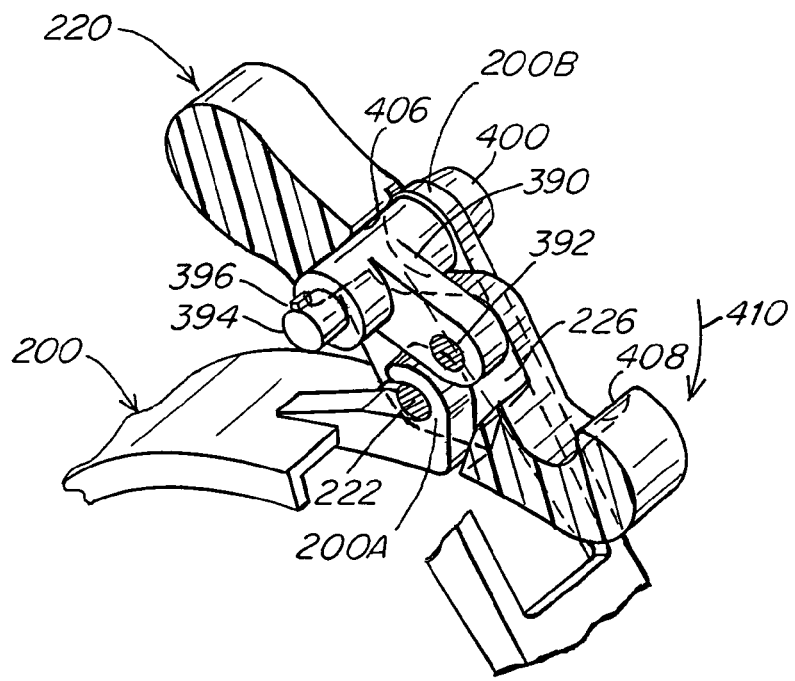
FIGS. 4A and 4B are further perspective views of respective positions of the release/lock lever.
Figure 4B:
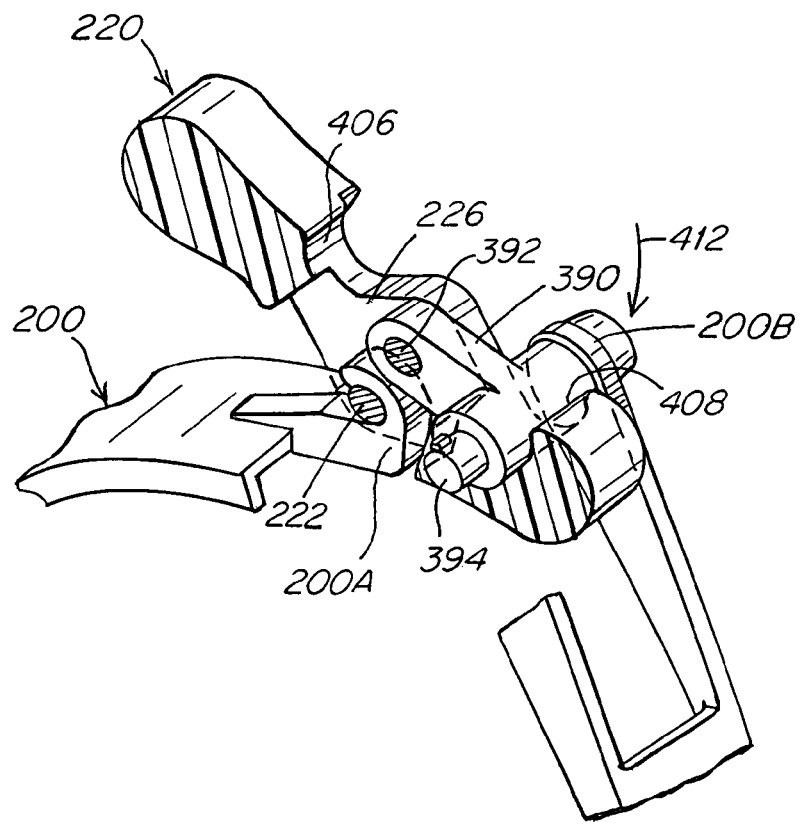

In the preferred embodiment of the instrument of the present invention there are actually considered to be three separate operational positions of the cinch ring 200. Also, a fully disassembled position of the cinch ring 200 is illustrated in FIG. 23. FIG. 4 shows the cinch ring in a locked first position in solid line. The phantom position shown in FIG. 4 and the position shown in solid line in FIG. 4A depict a second position in which the cinch ring has been sufficiently released so that the shaft angle can be changed or, alternatively, the cinch ring can be rotated for left or right hand use. From the position of FIG. 4A the link 390 can be rotated clockwise as seen in FIG. 4B to a third position which further relaxes the cinch ring enough for the disposable shaft portion to be removed from the handle portion with the cinch ring still loosely attached to the split hub, as in FIG. 15, or to the ball portion of the shaft, as in FIG. 18. The fourth position is shown in FIG. 23 where the cinch ring ends have been disconnected so It can be fully removed by itself from either the throw away shaft portion or from the handle portion.

Figure 27:
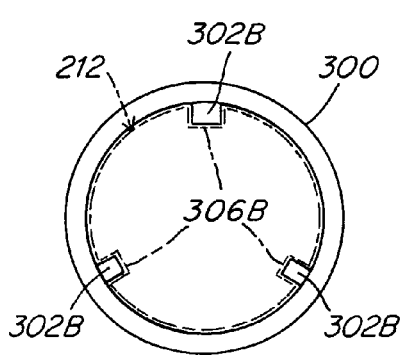
FIG. 27 is a schematic end view of a first alternate embodiment of an indexing means.
Figure 28:
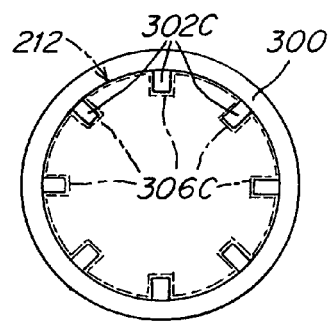
FIG. 28 is a schematic end view of a second alternate embodiment of an indexing means.

The connector 212 has an indexing feature that can be used to index the cables 100 to the rotation knob 24 and/or match shafts with different tools or end effectors to certain handles. As illustrated in FIGS. 8 and 24-26, the shaft receiver portion 300 of rotation knob 24 is provided with ribs 302 (see also FIG. 9) that mate with slots 306 on the outside surface of the connector 212. There is also preferably provided a tapered end 304 on each of the ribs 302 and a taper 216 on connector 212 to help align these members during assembly. Different rib patterns can be used as well as different thicknesses such as ribs 302A and slots 306A shown in FIG. 26. FIG. 27 schematically shows a pattern of three ribs 302B spaced 120 degrees apart in the receiver 300 mating with three equally spaced grooves 306B on the outside of the connector 212, shown in phantom outline. One set of ribs and grooves may be wider than the others as a further indexing feature. FIG. 28 depicts an arrangement of eight ribs 302C mating with eight slots 306C. When the connector is fully inserted in the receiver as shown in FIG. 3, the shoulder 308 on the connector 212 contacts seat 310 in the receiver and the cable crimps 102 sit in recess 312.

Figure 8:
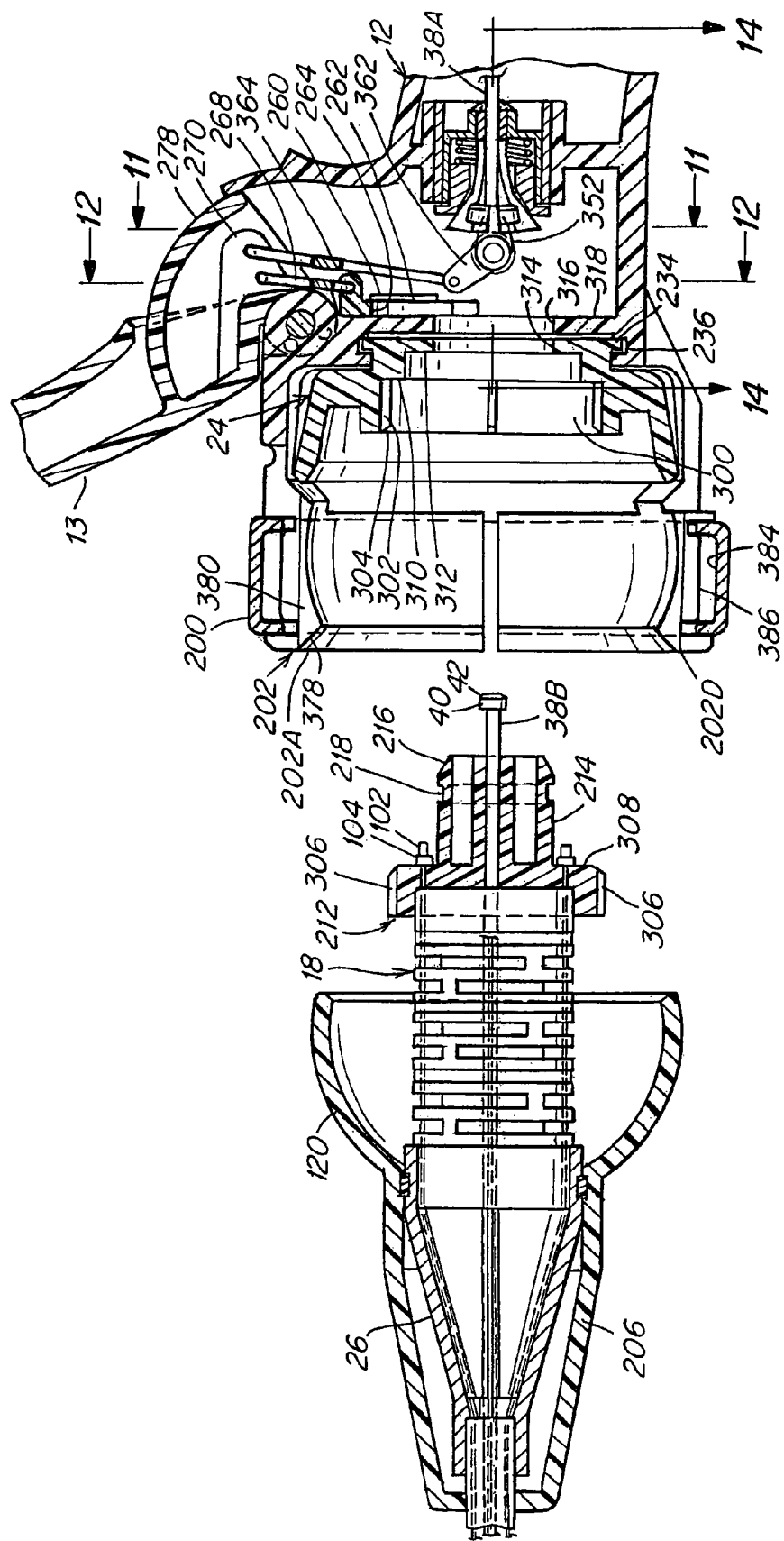
FIG. 8 is a cross-sectional view similar to that shown in FIG. 6 but with the instrument shaft portion being fully removed from the handle portion.

The rotation knob 24 is keyed to the proximal bending member 18 and when the rotation knob is rotated through rotation angle R1, the shaft portion 14 and proximal bending member rotate on bearings or bearing surfaces 208, 210. There is also a rotation on bearing surfaces between the clearance hole 316 against post 214. To retain the rotation knob and receiver portion in the correct position when the connector is absent there is provided a rim 234 on the proximal end of the rotation knob that fits loosely in the radial groove 236 in the handle halves, as shown in FIGS. 3 and 8.

Figure 12:
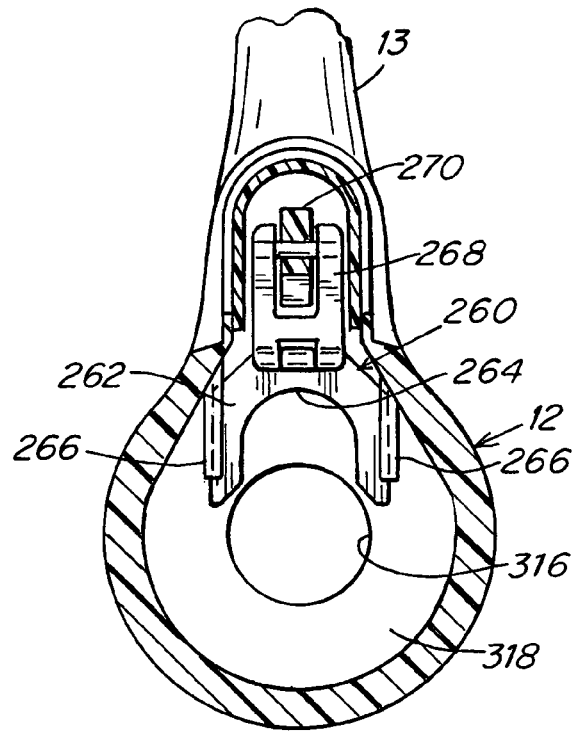
FIG. 12 is a cross-sectional end view of a means to lock the instrument shaft portion to the handle portion taken along line 12-12 of FIG. 8.

The shaft connector 212 is locked in place by actuation of shaft locking member or means 260 which include a gate 262 with a semi-circular rim 264 that loosely engages the groove 218 in the post 214 when the gate is in a down position. The gate 262 rides in slides 266 on wall 318. A link 268 pivotally connects the gate 262 to a lug 270 on the horn 13. When the horn is raised as shown in FIGS. 8 and 12, the rim 264 is clear of the groove 218 and the shaft connector is free to slide distally out of the receiver. The horn is hinged to the handle at pin 272 and has two positions as seen in respective FIGS. 3 and 5. There is a bump 274 on the horn that snaps into dimples 276 in the handle to hold the handle in either position. The horn structure includes a shroud 278 that closely fits the opening 280 in the handle to keep out contaminants. Other locking means may be used and may not be necessary if the split hub and cinch ring sufficiently contain the ball 120 within the split hub 202 when the lever 220 is in a relaxed position.

Figure 15:
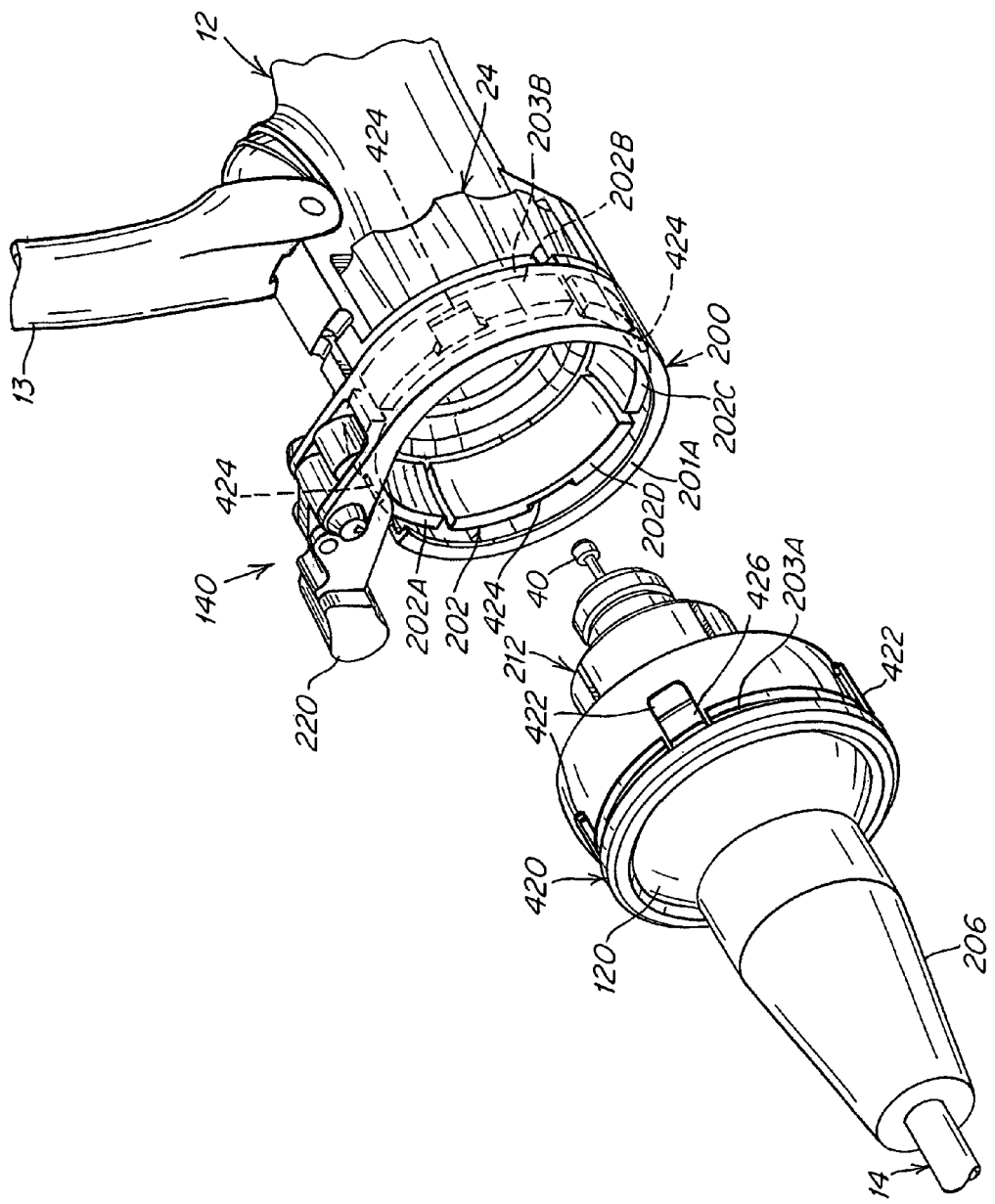
FIG. 15 is a fragmentary exploded perspective view of a second embodiment of a means to attach the instrument shaft to the handle portion.
Figure 16:
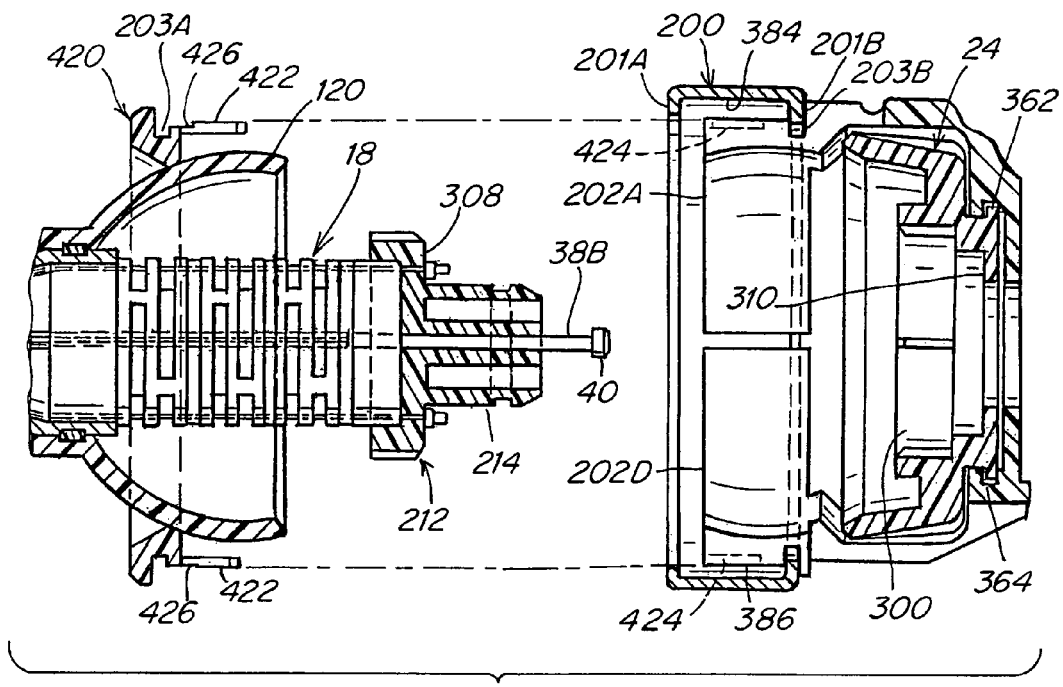
FIG. 16 is an exploded cross-sectional side view of the attachment means of FIG. 15.
Figure 17:
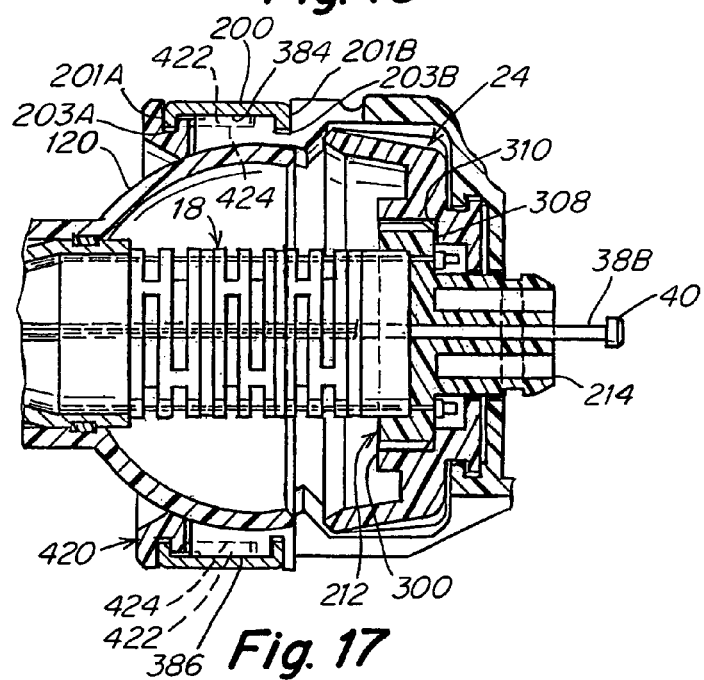
FIG. 17 is a cross-sectional side view of the embodiment illustrated in FIGS. 15 and 16 and showing the instrument shaft attached to the handle portion.

FIGS. 15-17 show an alternate means of attachment between the cinch ring, hub and shaft portion. In this embodiment the split hub may be separated from the shaft portion by means of a detachable front portion or ring 420 that is removed along with the shaft portion 14 and ball 120, as illustrated in FIG. 15-17. The ring 420 is shown as including a plurality of fingers 422 on the ring that each align with recesses 424 in the split hub. This arrangement provide alignment of the ring 420 with the split hub portions and the cinch ring flanges 201A and 201B with their respective grooves 203A and 203B. This construction also leaves a clearance space for the ends of the split hub portions 202A-202D enabling them to flex without binding against the proximal surface of the ring 420, as illustrated in FIG. 17. The fingers 422 are preferably attached to the ring 420 by living hinges 426 to allow them to flex with the split hub portions when the cinch ring 200 is tightened and the inside surface 384 of the ring exerts pressure on surfaces 386. The flanges 201 and grooves 203 are dimensioned so that the ring 420 can be removed from the split hub and cinch ring, but the cinch ring can't be removed from the split hub unless the ends 200A and 200B are disconnected (refer to FIGS. 21-23 for an illustration of the disconnection of the cinch ring itself).

Figure 18:
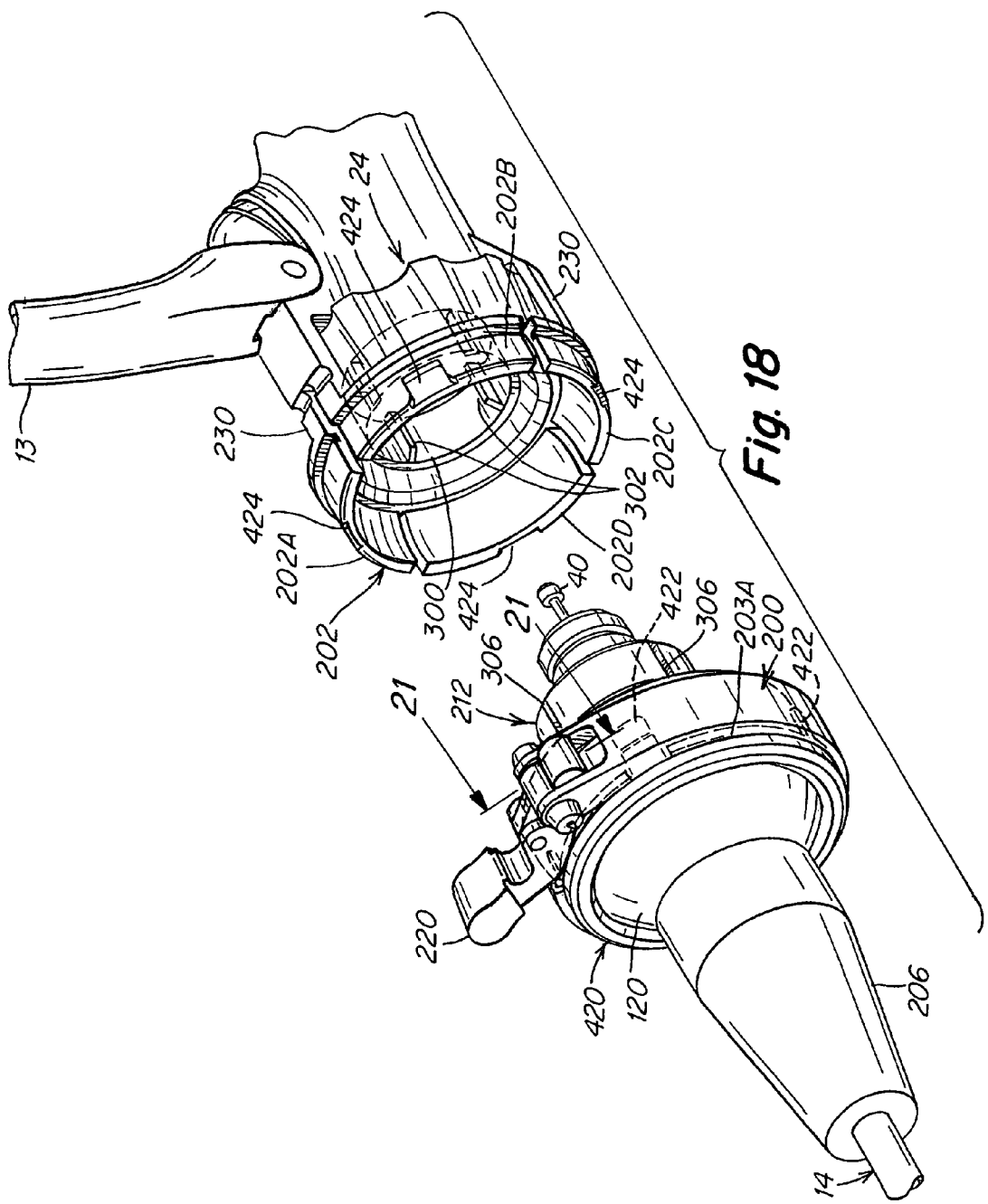
FIG. 18 is a fragmentary exploded perspective view of a third embodiment of a means for attaching the instrument shaft to the handle portion.
Figure 19:
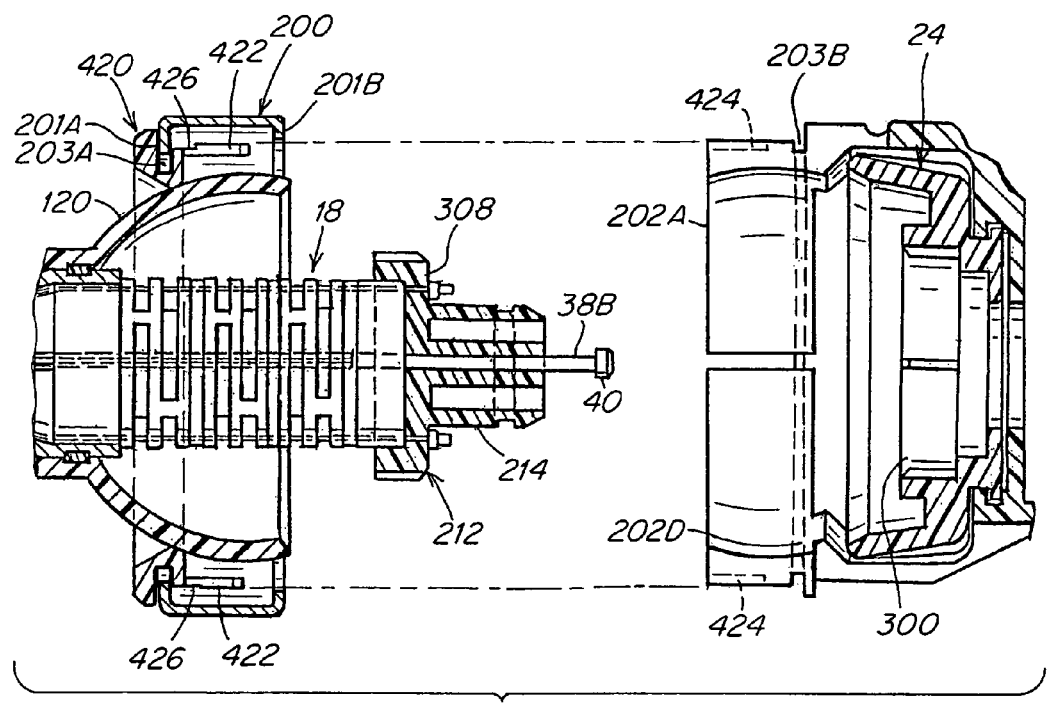
FIG. 19 is an exploded cross-sectional side view of the attachment means of FIG. 18.
Figure 20:
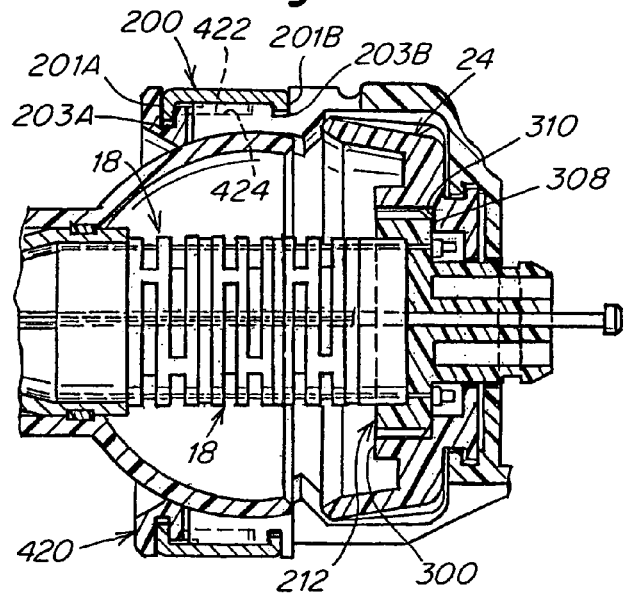
FIG. 20 is a cross-sectional side view of the embodiment illustrated in FIGS. 18 and 19 and showing the instrument shaft attached to the handle portion.
Figure 24:
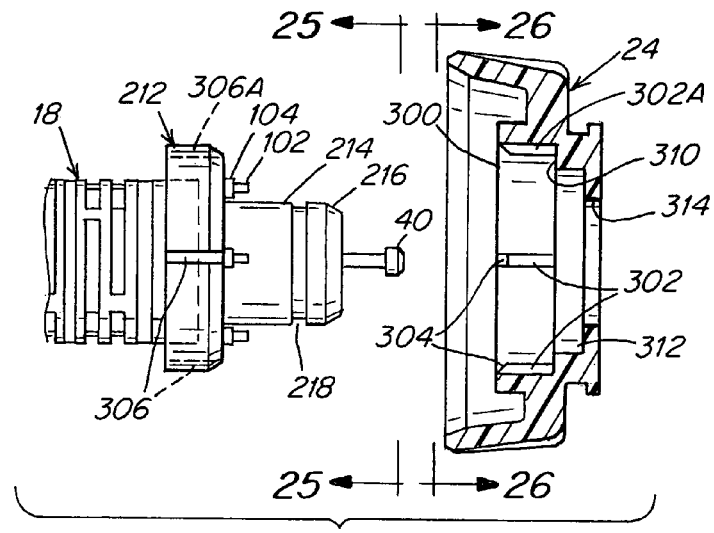
FIG. 24 is a fragmentary exploded side view of an indexing means to match the proper instrument shaft and end effector with the correct handle configuration.
Figure 25:
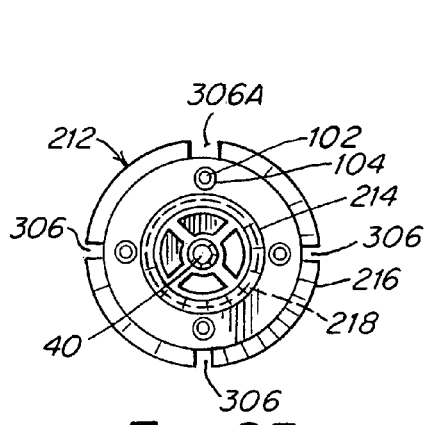
FIG. 25 is an end view of the proximal end of the instrument shaft as taken along line 25-25 of FIG. 24.
Figure 26:
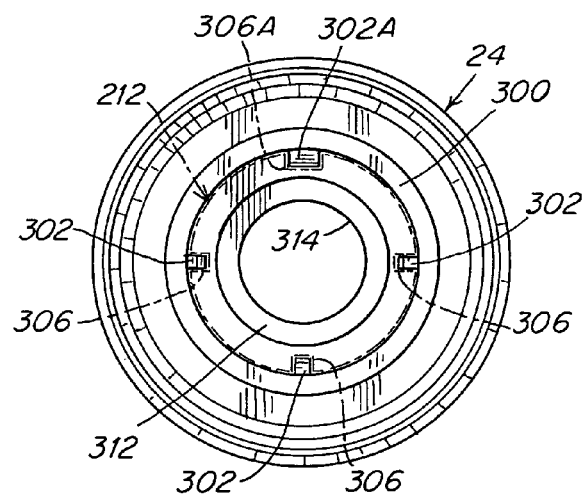
FIG. 26 is an end view of the distal end of the rotation knob and shaft receiver as taken along line 26-26.

Reference is now made to FIGS. 18-20 for still another embodiment for the connection and disconnection between the handle and shaft portions. The cinch ring 200 has different depth flanges 201A and 201B. The groove arrangement includes a groove 203A in the ring 420 and a groove 203B at the split hub. In this embodiment the flange 201A has a greater depth than the flange 201B so that the flange 201B may clear the groove 203B and allows the ring 420 to be removed along with the cinch ring 200 while retaining the cinch ring 200 on the ring 420, as illustrated in FIGS. 18 and 19. As shown in FIG. 23, the cinch ring 200 can be totally detached from both the ring 420 and the split hub by detaching ends 200A and 200B.

The angle locking member 140 is comprised primarily of the release/lock lever 220 which controls the length or outer circumference of the cinch ring 200. For a further explanation of the function of the lever 220 refer to the two cross-sectional views of FIGS. 4 and 7, as well as the two perspective views of FIGS. 4A and 4B. FIG. 4 depicts the instrument in the position where the shaft portion is fully engaged with the handle portion and the cinch ring is locked. FIG. 7 on the other hand depicts the instrument with the cinch ring at least partially released. In the later position an end 200B of the cinch ring 200 can be further released, as illustrated in FIG. 23.

As illustrated in FIG. 4, the lever 220 is pivoted at pin 222 which is connected to end 200A of the cinch ring. The end 200A is in the shape of a hook (see FIGS. 4A and 4B) and sits in a slot 226 in the lever. Pushing one end or the other of the lever 220 pivots the end 200B of the cinch ring 200 over the center line of the pivot pin 222 either tightening the cinch ring as shown in solid line in FIG. 4 or relaxing it as shown in phantom line in FIG. 4. In the solid line position of lever 220, the angle of the end effector is locked in place. When the lever 220 is pivoted in the direction of arrow 410 in FIG. 4 (see also FIG. 4A) the cinch ring 200 is relaxed as shown in the phantom line position in FIG. 4. In this relaxed or released position the angle of the end effector is free to be changed by rotation of the ball 120 in the split hub 202. Also, in the released position the cinch ring 200 maybe rotated in its grooves to allow a rotational adjustment of the position of the lever 220 for ease of use. Such an alternate rotational position is shown in the cross-sectional view of FIG. 7 wherein the cinch ring has been rotated clockwise from the position of FIG. 4. FIG. 7 also shows the lever 220 in its relaxed position.

The lever 220 supports a link 390 which sits in slot 226 and pivots about pin 392 at one end. The other end of the link 390 carries opposite posts 394 that pass through holes in the end 200B of the cinch ring 200. These posts are capped off by means of knobs 400. Knobs 400 retain the end 200B of the cinch ring 200 in a rotational relationship to the link 390 but end 200B can easily be released when the cinch ring is to be removed (see FIG. 22). The post and hole arrangement also provides a grip to rotate link 390 between stations 406 and 408. As shown in FIGS. 4B and 7, the link 390 has been rotated in the direction of arrow 412 from station 406 to station 408 which in effect loosens the cinch ring enough for the split hub to be expanded enough to remove the shaft and ball. From that position, the end 200B of the cinch ring can be removed by indexing the knobs 400 by means of indicators 401 (FIG. 23) in the direction of arrow 414 (FIG. 22) so that lugs 396 on the respective posts 394 line up with keyways 402 at the end 200B. Once aligned, the knobs 400 can be pulled outward in the direction of arrow 416 in FIG. 22 and end 200B can be detached as the recesses 398 in the knobs clear the posts 394. Rims 404 on the knobs prevent the knobs from detaching from the end 200B. The cinch ring 200 is then free to be completely removed from the split hub 202 and/or ring 420 as shown in FIG. 23.

In previous instrument constructions, the proximal bending member 18 has been mounted directly to the rotation knob 24 but now a connector 212 and receiver 300 allow the bending member 18 to be removed from rotation knob 24. The exploded cross-sectional view of FIG. 8 depicts the separation of the shaft portion 14 along with the proximal bendable member 18, ball 120 and connector 212 from the handle portion 12. The connector 212 is attached to the proximal end of the bendable member 18 and the cables 100 are illustrated as passing through the proximal bendable member 18 and connector 212. The cables terminate at the resilient pads 104 (or springs) and are crimped at 102. Thus, the proximal ends of the bend control cables are terminated at the connector 212. The connector 212 has a post 214 that passes through a clearance hole 314 in the rotation knob and a clearance hole 316 in the radial wall 318 of the handle. The post 214 has a taper 216 at its' proximal end to aid in assembly. The post 214 also has a circumferential groove 218 that is engaged by the shaft locking member or means 260. As depicted in FIG. 8, the proximal bendable member 18 and connector post 214 also carry the jaw actuation cable portion 38B in a central bore thereof. FIG. 8 also shows the cable end lug 40 that is attached to the very end of the cable portion 38B and extends outwardly from the post 214.

As indicated previously, the horn 13 is shown in its locked position in FIGS. 1 and 3 and is shown in its released position in FIGS. 2 and 5. As mentioned previously the pivoting of the horn causes the locking in of the shaft portion of the instrument relative to the handle portion thereof. Also, the pivoting of the horn is also used to control the inter-engagement between the cable portions by capturing the cable lug 40. This is accomplished by a clamping or releasing via a cable coupling member or means 320 which is illustrated in at least FIGS. 3, 10, 11, 13 and 14. The clamping member or means 320 includes a main collet member having plurality of jaws 322 each with recesses 324 that capture the lug 40 on the cable 38. The jaws are shown most clearly in the enlarged perspective view of FIG. 10. The jaws are disposed at the ends of respective spring arms 328 that are circumferentially disposed about the base 330 which may, in turn, be cemented to the handle portion 38A of cable 38. The jaws 322 are normally biased to an open position such as shown in FIG. 14 by means of the action of the spring arms 328.

Figure 13:
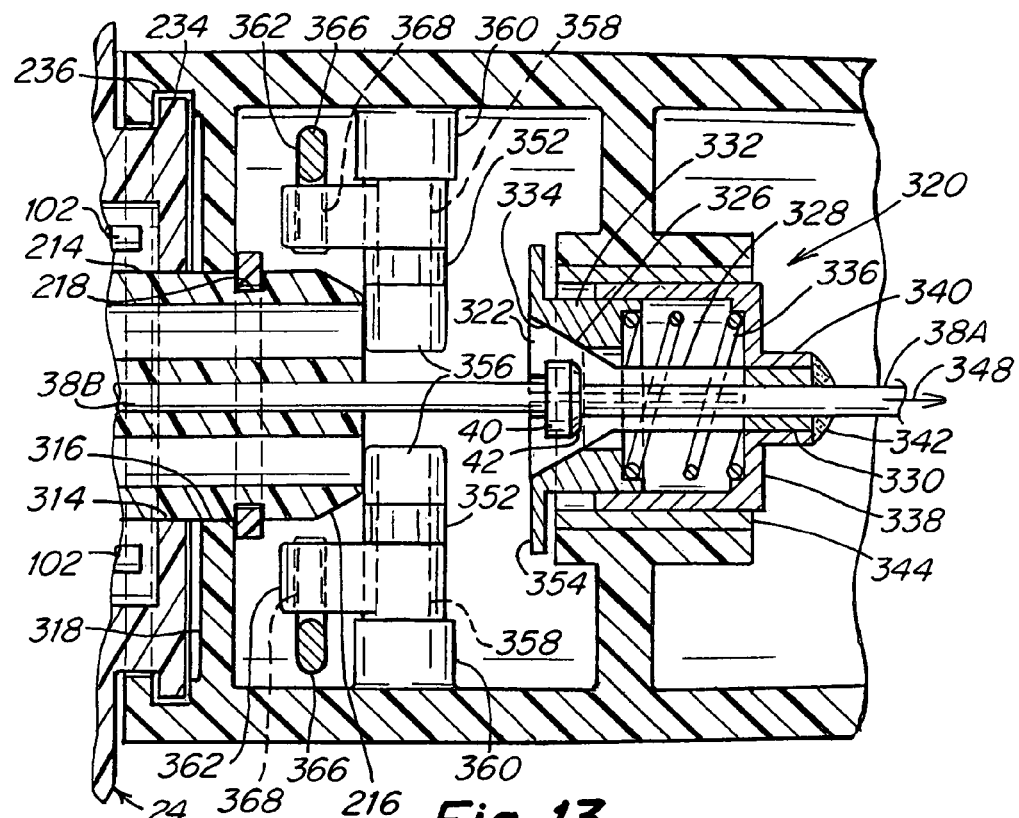
FIG. 13 is a cross-sectional plan view of the instrument shaft locking means and the cable coupling means engaged as taken along line 13-13 of FIG. 3 but showing the end effector cable being pulled as in use.

The jaws 322 of the clamping member 320 have ramped surfaces 326 on their outside surfaces that interact with the tapered surface 334 of the collet 332. This interaction controls the opening and closing of the clamping member. The collet 332 is normally urged distally by spring 336 that is loaded against the wall of the carriage 338 as illustrated in FIG. 13. The spring 336 is disposed in a pocket between a seat at the proximal end of the jaw members 322 and a seat in the carriage 338. The neck 340 of the carriage 338 is fixedly attached to the base 330 of the jaws 322, as well as to the cable portion 38B. This attachment may be by a number of different means such as by being cemented together. Refer to the cross-sectional view of FIG. 13 illustrating the cementing at 342.

The carriage 338 is adapted for sliding motion inside of the guide 344 which is, in turn, fixed to the handle 12. The guide 344 is supported by the sleeve 346 which is molded as part of the handle. In FIG. 13 the spring 336 is shown urging the collet 332, with its' tapered surface 334, against ramped surfaces 326 under the bias of the spring arms 328. This action maintains the jaws closed, thus capturing the cable lug 40 therein and essentially thus joining together the separate cable portions 38A and 38B. Once the cable portions are joined then the actuation cable functions as a single operable cable that is controlled from the proximal part of the instrument. The carriage 338 enables the cable to slide in performing its tool actuation function. The carriage 338 is shown as pulled proximally in the direction of arrow 348 in FIG. 13 to show the manner in which the carriage 338 with the closed jaws 322 is free to move proximally from the at rest position illustrated in FIG. 3.

Figure 14:
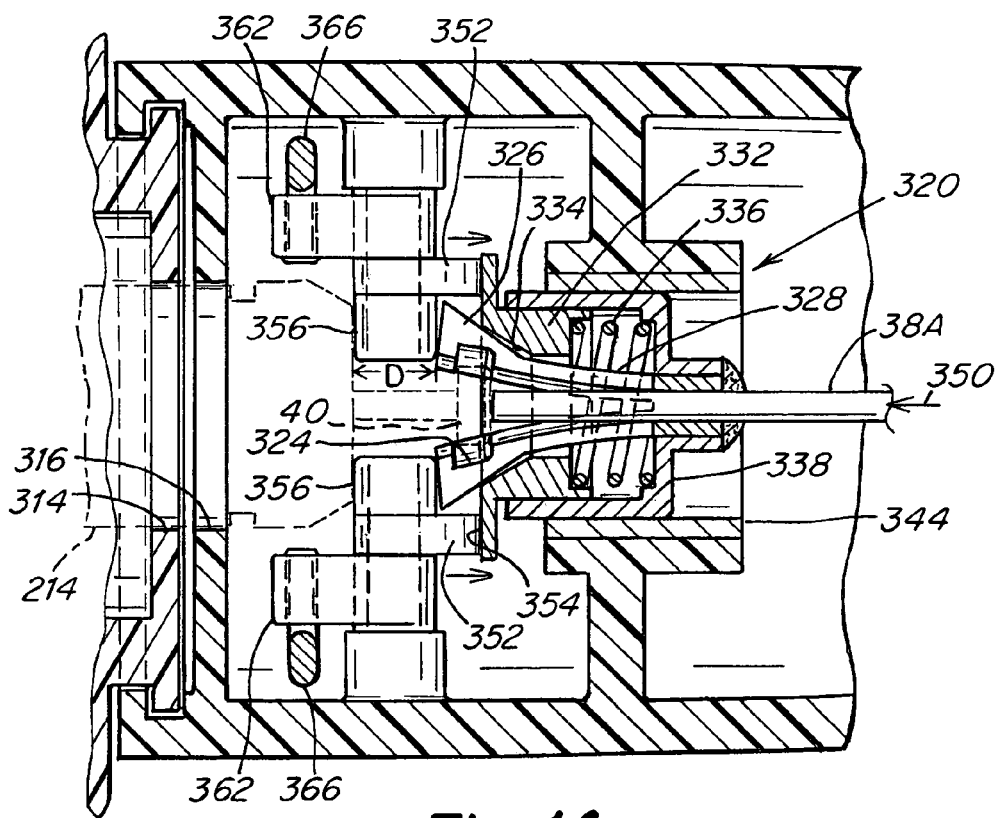
FIG. 14 is a cross-sectional plan view of the instrument shaft locking means and the cable coupling means in a released position as seen along line 14-14 of FIG. 8.

Refer now to FIG. 14 for an illustration of the release function which enables the shaft portion of the instrument to be separated or detached from the handle portion of the instrument. The jaws 322 are opened to release the lug 40 by the action of the cams 352 against the face 354 of the collet 332. The action of the cams 352 pushes the collet 332 proximally as illustrated in FIG. 14 to release the jaws from about lug 40. The spring arms 328 are constructed and arranged so as to normally urge the arms apart.

Figure 11:
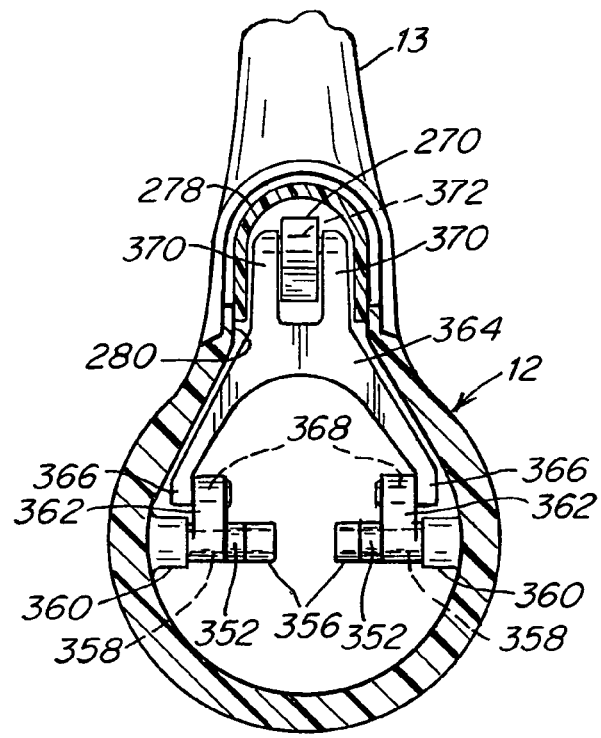
FIG. 11 is a cross-sectional end view of an actuation means for operating the coupling means of FIG. 10 taken along line 11-11 of FIG. 8.

FIG. 14 depicts a rest position of the instrument in which the slider 28 has normally urged the cable 38 in the direction of arrow 350. This action places the face of the jaws 322 against posts 356. This positioning ensures the proper alignment between the connector 212 and the cable coupling member 320. This assures alignment at the cable lug 40 when the horn 13 is either raised or lowered. Raising the horn lifts the lug 270 and along with it the pin 372 as illustrated in FIG. 11. This action pulls up on arms 366 of the yoke 364 which spread around the connector 212. Yoke 364 is supported at arms 370. Arms 366 carry pivot pins 368 that are attached to the arms 362 of posts 356 that are, in turn, mounted on pins 358 protruding from bosses 360 molded to the sides of the handle. The posts 356 act as stops for the proximal end of the shaft connector 212 and the face of the jaws 322. The posts 356 have cams 352 which engage and push against the face of the collet 354 when the horn 13 is raised, as depicted in FIG. 14.

Figure 29:
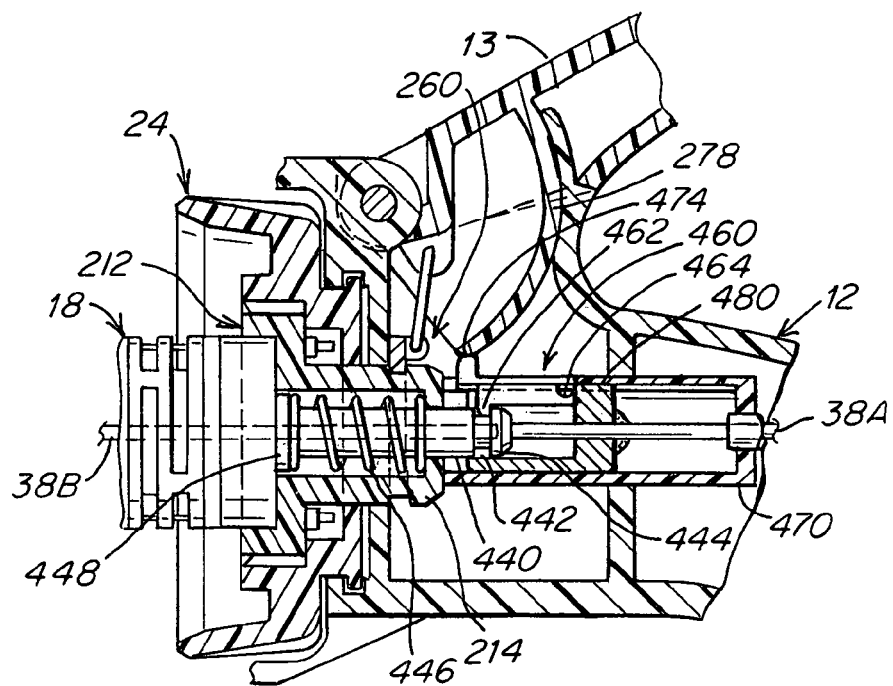
FIG. 29 is a fragmentary cross-sectional side view of an alternate embodiment of a cable coupling means.
Figure 30:
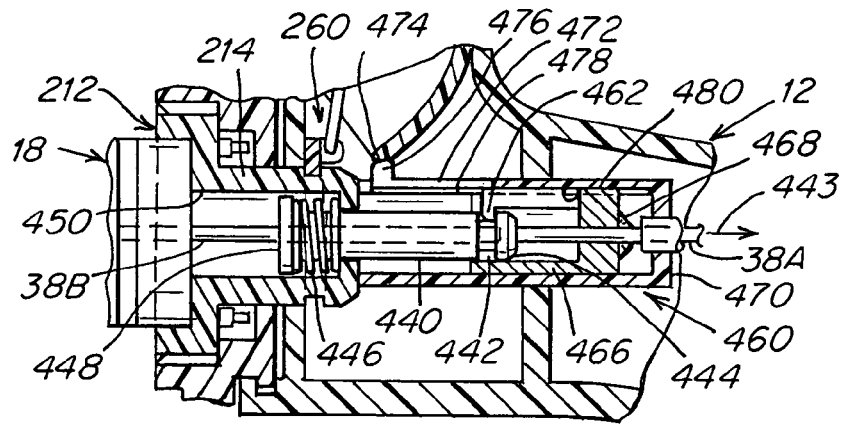
FIG. 30 is a cross-sectional view similar to that illustrated in FIG. 29 but showing the end effector cable being pulled as in use.
Figure 31:
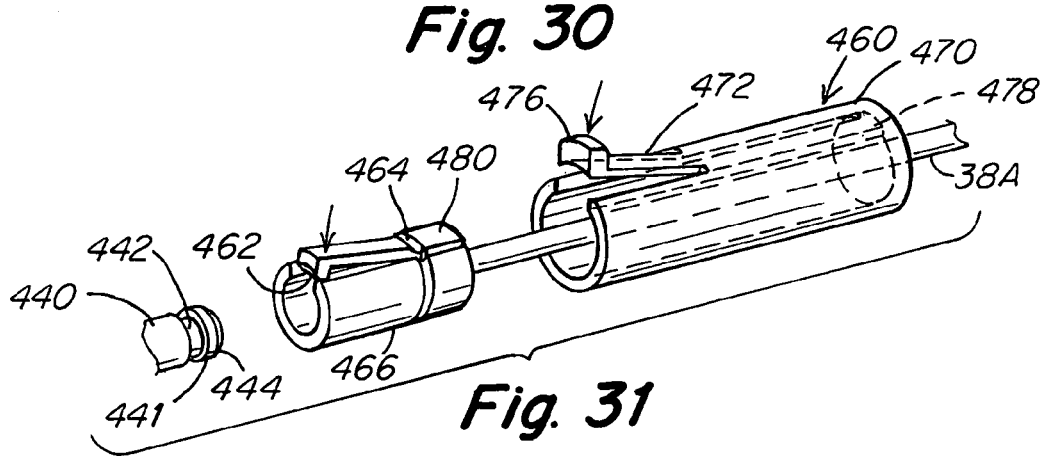
FIG. 31 is an exploded perspective view of the cable coupling means of FIG. 29.

An alternate embodiment of cable coupling member is shown in FIGS. 29-33, as coupling member 460. In this embodiment, the cable end lug 40 has been replaced with a spring loaded cable connector 440 that is contained in a passage 450 in the post 214 of the connector 212. A spring 446 biases the connector 440 distally to maintain the end effector jaws in an open position when the shaft portion 14 is removed. The spring 446 pushes flange 448 against the proximal end of the bendable member 18, such as depicted in FIG. 29. This eliminates a need for a sheath 46, as in FIG. 2, and helps keep the jaws open at an at rest position. Connector 440 has a tapered end 444 to aid in assembly and a groove 442 that can be captured by a finger 462 that is shown engaged in the position of FIGS. 29 and 30, and is normally biased to an open position as illustrated in FIG. 31.

Figure 32:
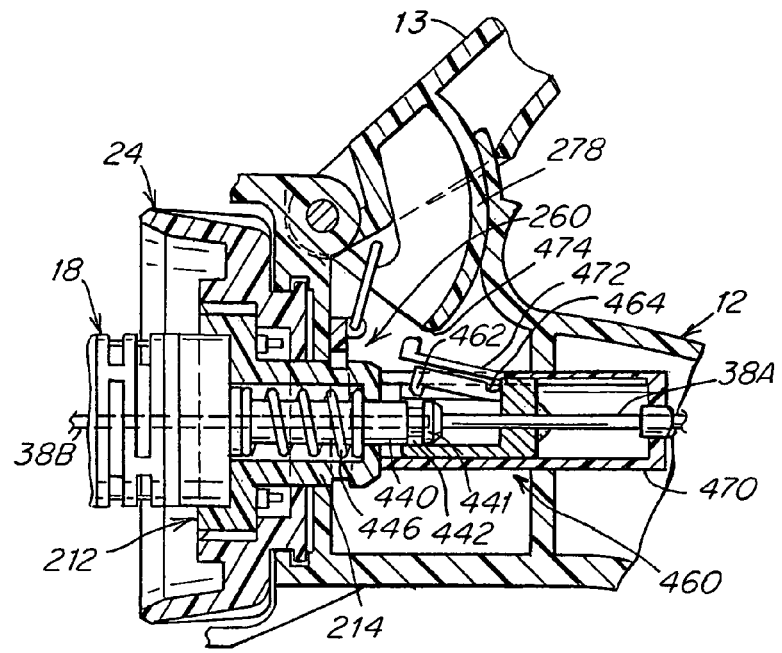
FIG. 32 is a cross-sectional view similar to that illustrated in FIG. 19 but showing the cable coupling means being released.
Figure 33:
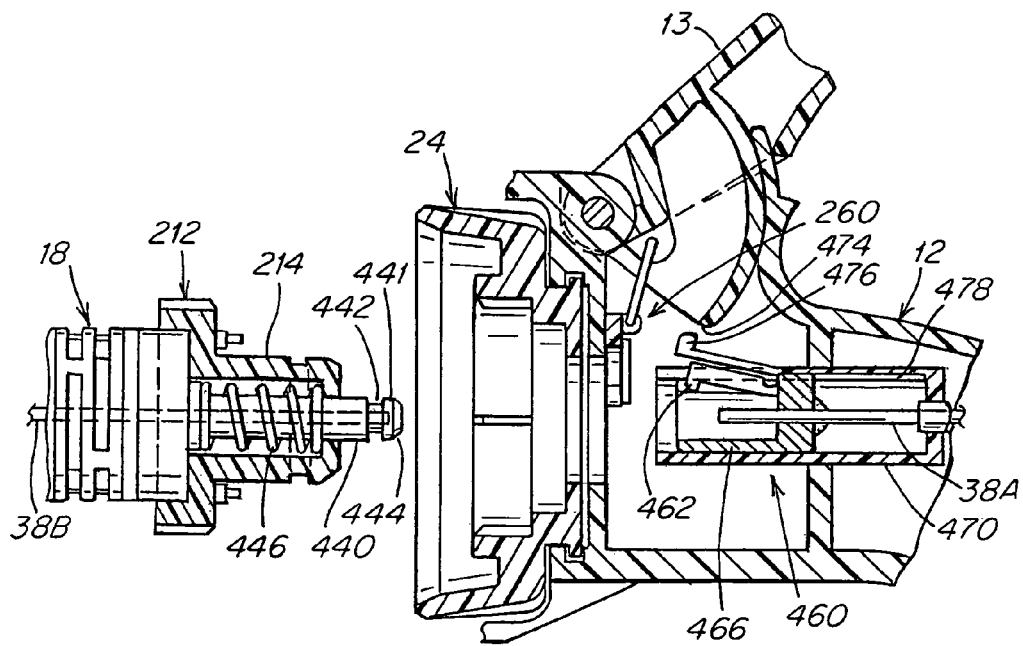
FIG. 33 is an exploded cross-sectional view of the embodiment of FIG. 32 and showing the instrument shaft portion removed from the handle portion.

The finger 462 is attached to sleeve 466 at a living hinge portion 464 that enables the finger 462 to flex inward when biased by flex arm 472 of the guide 470. Movement of the guide 470 over the sleeve 466 drops the finger 462 into groove 442 and thus captures the connector 440, as shown in FIG. 30. The finger 462 is molded as part of the sleeve 466 and has a key 480 that slides in keyway 478 of guide 470 to ensure proper alignment of the finger 462 and the flex arm 472. The sleeve 466 is cemented at 468 to the cable 38 and slides in the guide 470 which is attached to the handle 12. When the horn is raised, a cam surface 474 of the shroud 278 lifts off cam follower 476 on the end of the flex arm 472, allowing it to return to its at rest position as illustrated in FIG. 32. This allows the finger 462 to return to its at rest position thus releasing the connector 440. FIG. 33 is an exploded cross-sectional view of the embodiment of FIG. 32 and showing the instrument shaft portion removed from the handle portion. When the horn 13 is pushed down, the cam surface 474 pushes the flex arm 472 at the follower 476, and likewise pushes the finger 462 to the position shown in FIG. 29. This is a locked position for the cable coupler. The sleeve 466 functions as a carriage as depicted in FIG. 30 when the cable 38 is pulled by the slider 28.

FIGS. 29 and 30 both show the coupling lug 441 captured so that both proximal and distal portions of the actuation cable are interconnected. FIG. 29 shows more of an at rest position while FIG. 30 depicts the cable 38 pulled in the direction of arrow 443 so as to actuate the end effector. In FIG. 30 the sleeve is shown moved to the right and the spring 446 more compressed. FIG. 32 illustrates the horn having been raised to enable release of the distal portion of the instrument with the finger 462 and the flex arm 472 both released to a dis-engaged position. Finally, in FIG. 33 the shaft portion is shown separated from the handle portion.

FIGS. 34-38 show still a further alternate embodiment of a cable coupling member or means 500. In this embodiment, the connector 440 with its end lug 441 is inserted into a bore 518 in block 502 which also functions as a carriage. A spring loaded gate 504 with a keyhole shaped opening 506 is slidably mounted in transverse passage 507 of the block 502. The upper rim 508 of the keyhole opening is urged downward by spring 510 to engage groove 442 of the connector 440 in a rotational relationship. A neck 512 on the top of the gate 504 supports the spring 510 against a bracket 514 which, in turn, supports a stop 516 on the end of the neck 512. This arrangement ensures that the gate 504 does not drop out of the block 502 when there is no connector 440 present.

Figure 34:
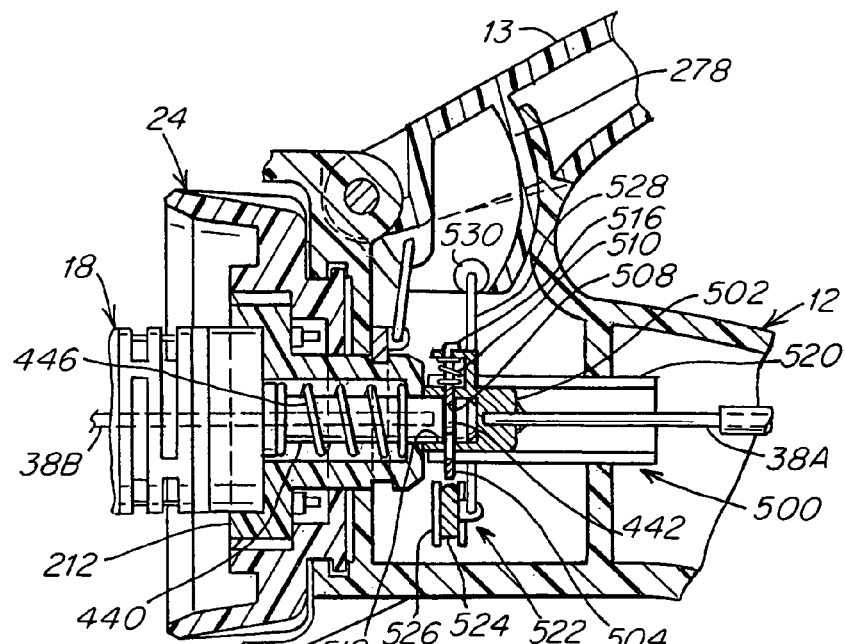
FIG. 34 is a cross-sectional side view of a further alternate embodiment of a cable coupling means.
Figure 35:
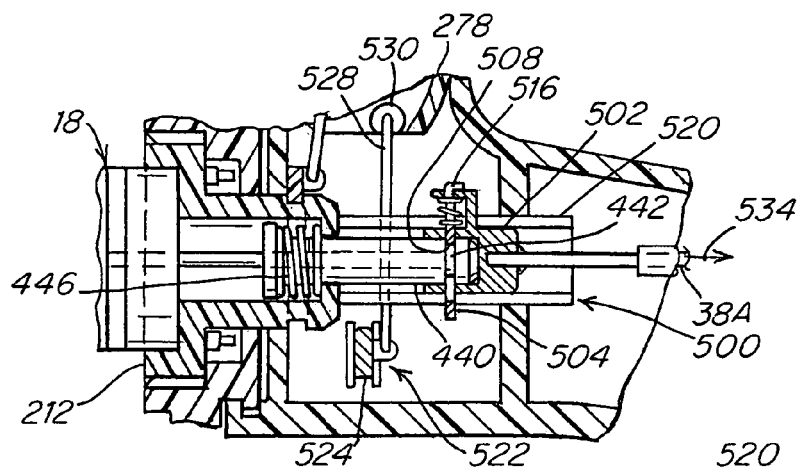
FIG. 35 is a cross-sectional view similar to that illustrated in FIG. 34 but showing the end effector cable being pulled as in use.
Figure 36:
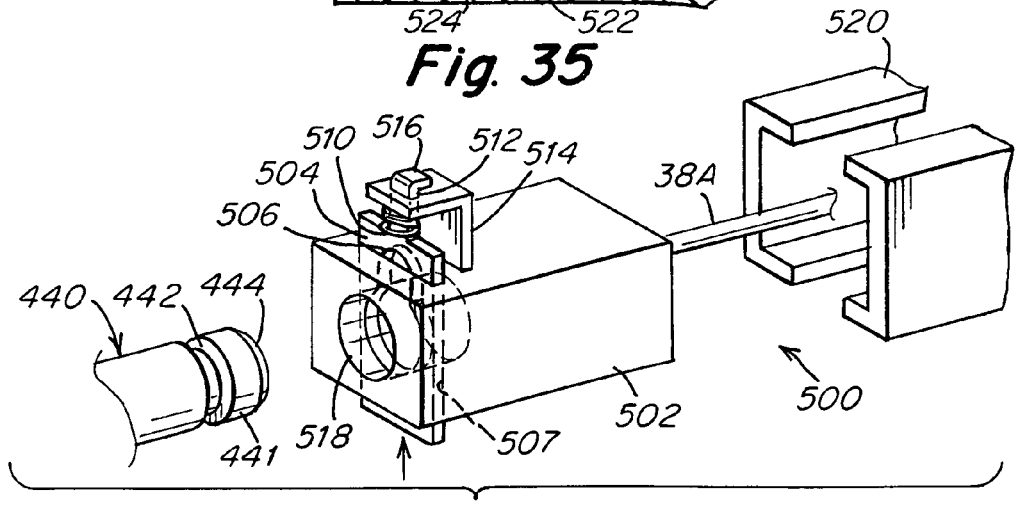
FIG. 36 is an exploded perspective view of the cable coupling means of FIG. 34.
Figure 37:
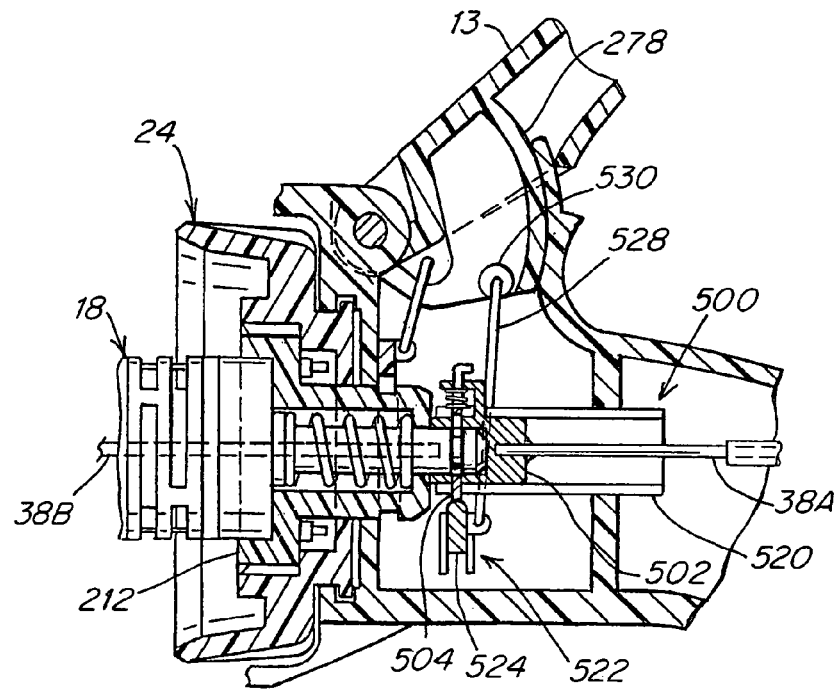
FIG. 37 is a cross-sectional view similar to that illustrated in FIG. 34 but showing the cable coupling means being released.
Figure 38:
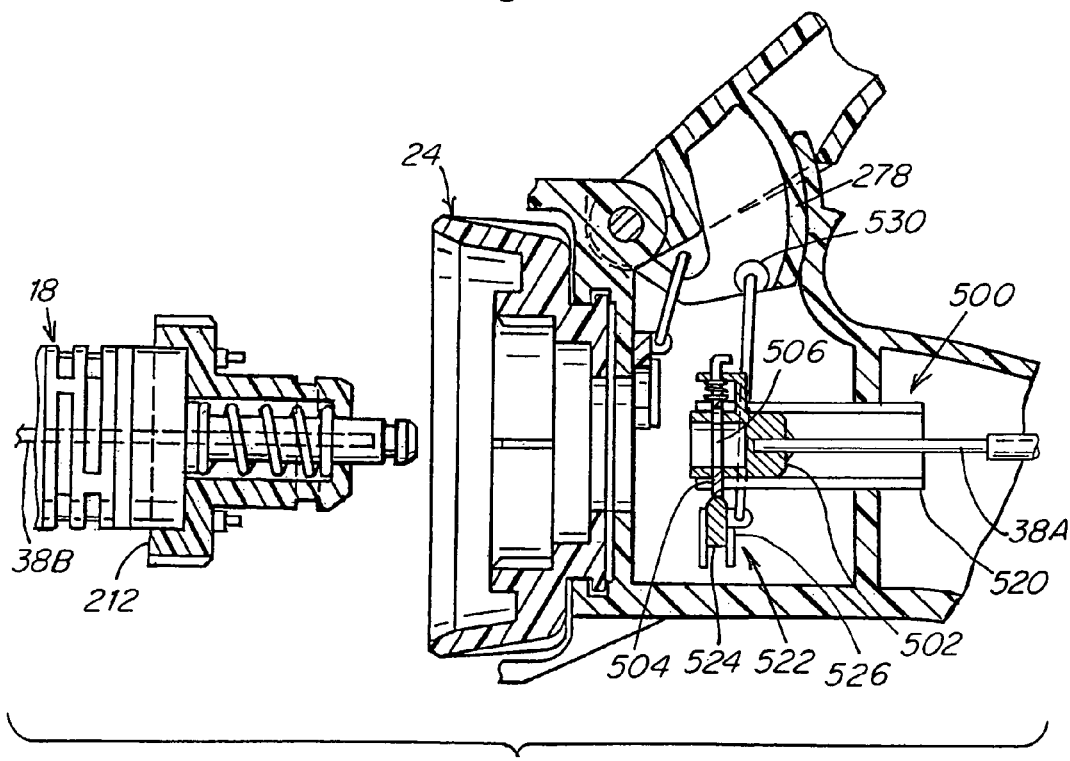
FIG. 38 is an exploded perspective view of the embodiment of FIG. 37 and showing the instrument shaft portion removed from the handle portion.

The carriage 502 travels in a slideway 520 which is affixed to the handle. A release means or member 522 is operated by rotating the horn. The member 522 includes a pusher 524 that riding in guides 526 and is connected to the horn 13 by link 528 which pivots in end bosses 530. The at rest position which is also the clamp/release position is shown in FIG. 34. The shaft portion is shown abutting the distal end of the fixed position slideway 520, the cable 38 is at rest, the spring 446 is at an extended position, the carriage 502 is at the distal end of the slideway 520 and the pusher 524 is shown lined up beneath the gate 504. In the cross-sectional view of FIG. 35 the connector 440 is clamped by means of the gate 504. FIG. 35 also illustrates the carriage 502 being pulled proximally, by arrow 534 by the cable 38 which, in turn, is connected to the slider 28. The spring 510 keeps the gate 504 down and latched but the connector 440 is free to rotate within block 502. FIG. 37 shows the horn raised and the pusher 524 in contact with and pushing up on the gate to align the wide portion of the keyhole opening 506 with the connector shaft so the connector 440 can be withdrawn as shown in FIG. 38.

After use of the surgical instrument of the present invention the used or contaminated shaft portion 14 can be easily detached from the handle portion 12 and disposed of as hereinafter described. In this regard reference is now made to the manner in which the shaft portion is readily detachable for the purpose of replacement thereof. For this explanation reference is made primarily to the first embodiment described herein. To release the shaft portion 14, the cinch ring 200 is released as shown in FIGS. 2 and 5 by manipulation of the angle locking means 140 to allow the split hub portions 202A-202D to be able to expand enough to allow clearance for the spherical ball 120. Once the cinch ring is released the spherical ball can be pulled out of the split hub 202 as the shaft portion 14 is withdrawn, and thus detached from the handle portion 12. Before detaching the shaft portion, the horn 13 is raised upward as shown in FIGS. 2 and 5, releasing both the shaft locking member 260 and the cable coupling member 320. The shaft portion 14 can then be grasped at the neck portion 206 of the ball 120 and pulled straight out of the handle portion 12 and disposed of. After sterilizing the handle portion 12, a new shaft portion 14 can be easily attached to it.

As shown in FIG. 2, the new shaft portion 14 may be fitted with a temporary sheath 46 that is semi-rigid and snugly fits over the end effector and the distal bending member 20 to hold the end effector jaws open which ensures that the lug 40 at the proximal end of the shaft portion 14 is fully inserted into the shaft connector 212. This is needed for proper alignment of the cable coupling means 320 and the lug 40 when the shaft portion 14 is inserted into the handle portion 12. The sheath 46 also holds the distal bending member 20 straight and thus the proximal bending member 18 straight with respect to the shaft and shaft connector 212 for correct alignment when the shaft portion 14 is inserted into the handle portion 12. There is also preferably provided an indexing means described herein in the form of ribs and grooves that ensure that the shaft connector 212 rotates in a fixed relationship to the rotation knob 24 and may also provide a matching means to ensure the correct matching of specific end effectors or tools to the proper handle configurations.

Next is described the step of insertion of a new shaft portion with the handle portion. As the shaft portion 14 enters the handle portion 12 the spherical surface 204 of the ball 120 contacts the beveled faces 378 of the respective split hub portions 202A-202D and forces them apart until the spherical surface 204 can clear the points created on the inside diameter of the split hub and the angled surfaces 380, as depicted in FIGS. 6 and 7. The angled surfaces 380 allow the spherical ball 120 to clear the split hub with less expansion of the portions 202A-202D to make it easier to slip the ball into and out of the split hub. The struts 230 that attach the split hub portions to the handle have thinned areas 382 that create living hinges that facilitate expansion of the split hub portions. FIG. 6, although previously described as illustrating removal of the shaft portion, can also be considered as illustrative of the relative positioning when the shaft portion 14 is inserted into the handle portion 12.

Continuing with the insertion step, next the post 214 of the shaft connector 212 is guided into the clearance hole 314 of the shaft receiver portion 300 of the rotation knob 24 and the clearance hole 316 in the wall 318 of the handle with the assistance of the tapered surface 216 at the free end of the post 214. The shaft 14 can be rotated until the indexing features, such as ribs 302 on the shaft receiver and grooves 306 on the shaft connector 212, mate under the urging of the split hub portions trying to return to a memory position and exerting a proximal pressure on the distal side of the spherical ball 120. The ribs 302 are tapered at 304 and the connector 212 is tapered at 216 to assist in the alignment. Once properly aligned, the shaft connector 212 can slide proximally until the shoulder 308 on the connector contacts the seat 310 of the shaft receiver portion 300 as depicted in FIG. 5.

There is provided a recess 312 in the shaft receiver 300 to allow clearance for the terminal wire crimps 102 and resilient pads 104. As the connector seats in the receiver, the cable connection lug 40 is guided into the cable coupling jaws 322 guided by the taper 42 on the lug. When the connector 212 is fully seated in the receiver 300 the end of the post 214 abuts and contacts one side of the posts 356, as illustrated in FIG. 14. The faces of the jaws 322 abut the other side of the posts 356 as urged by the carriage spring 336. FIG. 14 also shows that the proper distance D is provided that ensures that the lug 40 is abutting and preferably contacting the portion of the cable 38 that is attached to the slider 28. Also, this positioning provides alignment of the lug 40 with the recesses 324 in the jaws 322 so that when collet 332 is released, the jaws 322 capture the lug 40.

Once the shaft portion is properly seated then the shaft portion 14 is now ready to be locked to the handle. The horn 13 is rotated clockwise or downwardly to the position depicted in FIG. 3. This releases the collet 332 and the jaws 322 capture the lug 40 while the shaft locking means 260 locks the shaft connector 212 in a rotational relationship with respect to the handle. The cinch ring 200 is then tightened by the release/lock lever 220 and the sheath 46 can be removed while gently squeezing the jaw clamping lever 22 while pulling on the distal end of the sheath. The instrument is now ready for use.

Having now described a limited number of embodiments relating to the principles of the present invention, it should now be apparent to one skilled in the art that numerous other embodiments and modifications thereof are contemplated as falling within the scope of the present invention, as defined by the appended claims. For example, although the horn member has been described as the means by which the cable coupling is initiated, it is to be understood that other existing instrument members or added members may be used to initiate this action. In one other example the tool actuation lever may be adapted for the cable coupling function.

What is claimed is:

1. A surgical instrument comprising:
an instrument shaft having proximal and distal ends and a longitudinal axis;
a tool disposed from the distal end of the instrument shaft;
a control handle coupled from the proximal end of the instrument shaft;
a distal motion member for coupling the distal end of said instrument shaft to said tool;
a proximal motion member for coupling the proximal end of said instrument shaft to said handle;
actuation cabling extending between said distal and proximal motion members for coupling motion of said proximal motion member to said distal motion member for controlling the positioning of said tool;
a rotation knob disposed between the control handle and proximal motion member and rotatable relative to the control handle for causing a corresponding rotation of the tool about a distal tool roll axis, wherein the distal tool roll axis is different than the longitudinal axis of the instrument shaft;
and a locking mechanism for fixing the position of the tool at a selected position and having locked and unlocked states;
said locking mechanism including a ball and socket arrangement disposed about at least a part of said proximal motion member;
and an actuation cable extending from said handle to said tool for controlling the actuation of the tool;
said actuation cable separated into two inter-engagable cable segments that enable the proximal motion member to be disconnected from the control handle.

2. The surgical instrument of claim 1 wherein said ball and socket arrangement including a socket member having an inner partially spherical shaped surface, and a ball member having an outer partially spherical shaped surface that mates with the partially spherical shaped socket surface so as to enable motion between the ball member and the socket member.

3. The surgical instrument of claim 2 wherein said locking mechanism further includes a manually operable locking lever mounted at the control handle and that, when moved to the locked state, provides a locking between the socket member and the ball member so as to fix the relative position between the socket member and the ball member to, in turn, fix the position of the tool.

4. The surgical instrument of claim 1 including an actuation lever supported from said handle at a pivot point on the handle and for controlling the actuation cable.

5. The surgical instrument of claim 1 including a slider for capturing the proximal end of said tool actuation cable and an actuation lever supported at said handle for controlling the translation of said slider and, in turn, the operation of said tool.

6. The surgical instrument of claim 1 wherein said locking mechanism further includes a cinch member for locking said ball and socket arrangement.

7. The surgical instrument of claim 6 wherein the ball and socket arrangement comprises a ball member and a socket member that comprises a split socket and said cinch member closes said split socket to lock the socket member on the ball member.

8. The surgical instrument of claim 1 including a horn that is pivotally supported from the handle and that is operable to engage and disengage the cable segments.

9. The surgical instrument of claim 8 including a collet supported in the handle for closing about the cable segments.

10. In a medical instrument having a proximal control handle and a distal tool that are intercoupled by an elongated instrument shaft having a longitudinal axis and being meant to pass internally of an anatomic body, proximal and distal movable members that respectively intercouple said proximal control handle and said distal tool with said instrument shaft, cable control means disposed between said movable members so that a motion at said proximal movable member controls said distal movable member and, in turn, the distal tool, an actuation member at said handle for controlling said distal tool, a rotation knob disposed between the control handle and proximal movable member and rotatable relative to the control handle for causing a corresponding rotation of the tool about a distal tool roll axis that is different than the longitudinal axis of the instrument shaft, and a locking mechanism for fixing the position of the tool at a selected position and having locked and unlocked states, said locking mechanism including a ball and socket arrangement disposed about at least a part of said proximal movable member, and a coupler for selectively engaging or disengaging separable cable segments of the actuation member.

11. The medical instrument of claim 10 wherein said coupler includes a collet attached to one of said cable segments and a capture lug on the other of the cable segments, said collet for retaining said capture lug to engage the cable segments.

12. The medical instrument of claim 11 including a pivot member on the handle including at least one link that is operable to control a cam that sets open and closed positions of the collet.

13. The medical instrument of claim 12 wherein said pivot member forms a horn at the top of the handle to assist in a comfort grip of the handle.

14. The medical instrument of claim 13 wherein said collet includes a quick disconnect mechanism having a base in which the collet is positioned and a spring that biases the base to a closed position of the collet.

15. An instrument having a proximal control handle and a distal tool that are intercoupled by an elongated instrument shaft having a longitudinal axis, proximal and distal movable members that respectively intercouple said proximal control handle and said distal tool with said instrument shaft, cabling disposed between said movable members so that a motion at said proximal movable member controls said distal movable member and, in turn, the distal tool, a rotation knob disposed between the control handle and proximal motion member and rotatable relative to the control handle for causing a corresponding rotation of the tool about a distal tool roll axis that is different than the longitudinal axis of the instrument shaft, and a locking mechanism for fixing the position of the tool at a selected position and having locked and unlocked states, said locking mechanism including a ball and socket arrangement disposed about at least a part of said proximal motion member, a tool actuation member supported at the handle for controlling the distal tool including a tool control cable that extends between the handle and distal tool, said tool control cable including separate control cable segments that are adapted to have one of an engaged state and a dis-engaged state.

16. The instrument of claim 15 wherein said ball and socket arrangement including a socket member having an inner partially spherical shaped surface, and a ball member having an outer partially spherical shaped surface that mates with the partially spherical shaped socket surface so as to enable motion between the ball member and the socket member.

17. The instrument of claim 15 wherein the proximal motion member can be disconnected from the control handle when the control cable segments are in their dis-engaged state.

18. The instrument of claim 17 including a coupler for selectively engaging or disengaging the separable cable segments.

19. The instrument of claim 17 wherein said coupler includes a collet attached to one of said cable segments and a capture lug on the other of the cable segments, said collet for retaining said capture lug to engage the cable segments.

20. The instrument of claim 19 wherein said collet includes a quick disconnect mechanism having a base in which the collet is positioned and a spring that biases the base to a closed position of the collet.

21. The instrument of claim 15 wherein said ball and socket arrangement includes a socket member having an inner partially spherical shaped surface, and a ball member having an outer partially spherical shaped surface that mates with the partially spherical shaped socket surface so as to enable motion between the ball member and the socket member, and said locking mechanism further includes a manually operable locking lever mounted at the control handle and that, when moved to the locked state, provides a locking between the socket member and the ball member so as to fix the relative position between the socket member and the ball member to, in turn, fix the position of the tool.

22. The instrument of claim 15 wherein said tool actuation member includes an actuation lever supported from said handle at a pivot point on the handle and for controlling the tool control cable.

23. The instrument of claim 15 including a slider for capturing the proximal end of said tool control cable and an actuation lever supported at said handle for controlling the translation of said slider and, in turn, the operation of said tool.

24. The instrument of claim 16 wherein said locking mechanism further includes a cinch member for locking said ball and socket arrangement.

25. The instrument of claim 24 wherein said cinch member comprises a cinch ring that is disposed about the socket member, and said socket member comprises a split hub.

26. The instrument of claim 15 wherein the ball and socket arrangement comprises a ball member and a socket member that comprises a split hub and said cinch member comprises a cinch ring disposed about the split hub so as to close the split hub to lock the socket member relative to the ball member.

27. The instrument of claim 15 including a horn that is pivotally supported from the handle and that is operable to engage and disengage the cable segments.

28. The instrument of claim 15 including a coupler for selectively engaging or disengaging the separable cable segments, said coupler comprised of a cable connector on one of said cable segments and an engagement sleeve on the other of the cable segments.

29. The instrument of claim 28 including a tubular coupling member receiving said sleeve, said tubular coupling member having a cam follower activated from a manually operated control lever, said cable connector having a groove, said sleeve having a finger engaged by the cam follower for connecting with said groove in the engaged state.

30. The instrument of claim 29 wherein the manually operated control lever includes a pivot horn on the control handle.

31. The instrument of claim 15 including a coupler for selectively engaging or disengaging the separable cable segments, said coupler comprised of a cable connector on one of said cable segments and a carriage on the other of the cable segments.

32. The instrument of claim 31 including a slideway for receiving said carriage, and an engagement door supported by said carriage and activated from a manually operated control lever, said cable connector having a groove, said door for connecting with said groove in the engaged state by sliding engagement with said groove.

33. The instrument of claim 32 wherein the manually operated control lever includes a pivot horn on the control handle, and further including a release member operated by pivoting the horn.

* * * * *